(12) United States Patent
Rezai et al.

(10) Patent No.: US 8,454,571 B2
(45) Date of Patent: Jun. 4, 2013

(54) DISPOSABLE ABSORBENT ARTICLE HAVING A FRANGIBLE BONDING AGENT

(75) Inventors: Ebrahim Rezai, Mason, OH (US); Shunketsu Sue, Mason, OH (US); Stephen Joseph Lange, Cincinnati, OH (US); Mark James Kline, Okeana, OH (US); James David Landgrebe, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 434 days.

(21) Appl. No.: 12/794,103

(22) Filed: Jun. 4, 2010

(65) Prior Publication Data

US 2010/0312207 A1 Dec. 9, 2010

Related U.S. Application Data

(60) Provisional application No. 61/184,102, filed on Jun. 4, 2009.

(51) Int. Cl.
 *A61F 13/15* (2006.01)
(52) U.S. Cl.
 USPC ........... 604/391; 604/389; 604/396; 604/387; 604/394
(58) Field of Classification Search
 USPC ................... 604/391, 389, 396, 387, 394
 See application file for complete search history.

(56) References Cited

U.S. PATENT DOCUMENTS

| | | | |
|---|---|---|---|
| 4,662,875 A | 5/1987 | Hirotsu |
| 4,673,402 A | 6/1987 | Weisman |
| 4,738,677 A | 4/1988 | Foreman |
| 4,834,735 A | 5/1989 | Alemany |
| 4,846,815 A | 7/1989 | Scripps |
| 4,888,231 A | 12/1989 | Angstadt |
| 4,894,060 A | 1/1990 | Nestegard |
| 5,021,051 A | 6/1991 | Hiuke |
| 5,032,122 A | 7/1991 | Noel |
| 5,092,861 A | 3/1992 | Nomura |
| 5,147,345 A | 9/1992 | Young |
| 5,234,423 A | 8/1993 | Alemany |
| 5,246,433 A | 9/1993 | Hasse |
| 5,256,717 A | 10/1993 | Stauffer |
| 5,326,612 A | 7/1994 | Goulait |
| 5,569,234 A | 10/1996 | Buell |
| 5,611,789 A | 3/1997 | Seth |
| 5,897,545 A | 4/1999 | Kline |
| 5,957,908 A | 9/1999 | Kline |

(Continued)

FOREIGN PATENT DOCUMENTS

| | | |
|---|---|---|
| WO | WO 92/22273 | 12/1992 |
| WO | WO 96/04812 | 2/1996 |

(Continued)

OTHER PUBLICATIONS

PCT International Search Report, PCT/US2010/037406 date of mailing Jun. 10, 2010.

*Primary Examiner* — Jacqueline F. Stephens

(74) *Attorney, Agent, or Firm* — Kathleen Y. Carter; John G. Powell

(57) ABSTRACT

A disposable absorbent article that includes a frangible bonding agent for maintaining the absorbent article in a predetermined configuration. The frangible bonding agent may be disposed on a fastening system in order to maintain one or more portions of the fastening system in a particular position during manufacturing but still provide an easy-to-open fastener when used by a consumer.

32 Claims, 15 Drawing Sheets

U.S. PATENT DOCUMENTS

| | | |
|---|---|---|
| 6,120,487 A | 9/2000 | Ashton |
| 6,120,489 A | 9/2000 | Johnson |
| 6,432,098 B1 | 8/2002 | Kline |
| 6,940,464 B2 | 9/2005 | Petersson |
| 7,416,545 B1 | 8/2008 | Kline |
| 7,717,150 B2 | 5/2010 | Manabe |
| 2005/0208854 A1 | 9/2005 | Sadato |
| 2006/0027320 A1 | 2/2006 | Kueppers et al. |
| 2008/0004591 A1 | 1/2008 | Desai et al. |
| 2008/0044616 A1 | 2/2008 | Hanao |
| 2008/0050555 A1 | 2/2008 | Sadato |
| 2008/0262459 A1 | 10/2008 | Kamoto |
| 2008/0312627 A1 | 12/2008 | Takeuchi |
| 2009/0004435 A1 | 1/2009 | Hanao |
| 2010/0191211 A1 | 7/2010 | Molander |

FOREIGN PATENT DOCUMENTS

| | | |
|---|---|---|
| WO | WO 96/22065 | 7/1996 |
| WO | WO 98/22069 | 5/1998 |
| WO | WO 99/11211 | 3/1999 |
| WO | WO 99/11212 | 3/1999 |
| WO | WO 00/27329 | 5/2000 |
| WO | WO 03/105740 | 12/2003 |
| WO | WO 2007/036908 | 4/2007 |
| WO | WO 2007/069227 | 6/2007 |
| WO | WO 2007/072386 | 6/2007 |
| WO | WO 2007/072421 | 6/2007 |
| WO | WO 2007/096841 | 8/2007 |
| WO | WO 2007/096842 | 8/2007 |

DISPOSABLE ABSORBENT ARTICLE HAVING A FRANGIBLE BONDING AGENT

CROSS REFERENCE TO RELATED APPLICATIONS

This application claims the benefit of U.S. Provisional Application No. 61/184,102, filed Jun. 4, 2009.

FIELD OF THE INVENTION

A configuration for packaging a disposable absorbent article is disclosed. More specifically, a disposable absorbent article is maintained in a particular configuration by a frangible bonding agent to facilitate packaging and/or subsequent use of the absorbent article.

BACKGROUND OF THE INVENTION

Wearable absorbent articles (e.g., taped diapers, pull-on diapers, training pants, sanitary napkins, panty liners, incontinence briefs, and bandages) typically offer the benefit of receiving and containing the bodily exudates of a wearer. Disposable varieties of such absorbent articles are commonly known, and are typically mass produced on a high speed production line. Some disposable absorbent articles include a mechanical fastening system (e.g., hook/loop or tab/slot) for maintaining the article in a desired position or configuration prior to, during, and/or after use of the article. Such fastening systems may include one or more elements that extend laterally outwardly beyond the side edges of the article, such as commonly known fastening tabs. These laterally outwardly extending portions of the fastening system may increase the risk of contamination or damage to the article, an article element, and/or the manufacturing equipment during a high speed manufacturing process. Repositioning the outwardly extending portions of the fastening system (e.g., by folding the portion laterally inward) may reduce the likelihood of damage or contamination, but the folded fastening system element may not remain suitably folded for a desired amount of time (e.g., the duration of the manufacturing process) due to the high speed nature of the manufacturing process.

A fastening system that includes a mechanical fastener having commonly known hooks or other similar features may be maintained in a folded configuration by engaging the mechanical fastener with a complementary element of the fastening system, such as loops or a nonwoven portion. Such mechanical fastening systems are generally engaged by entangling the hooks or other similar feature with the complementary element. However, an engaged mechanical fastening system still may not provide sufficient bonding strength to maintain the fastening system in the desired folded configuration during a high speed manufacturing process. Therefore, in order to increase the bond strength of the mechanical fastener, a bonding agent such as an adhesive may be applied to one or more portions of the mechanical fastener prior to folding and/or engaging the fastening system. Conventional adhesives such as commonly known pressure sensitive adhesives generally form permanent bonds. The bond strength provided by at least some permanent bonding agents such as commonly known hot-melt adhesives typically remain substantially constant or may even increase between the time the absorbent article is made and the time it is purchased and/or used by a consumer. For example, during shipping and/or storage of disposable absorbent articles, the articles may be subjected to a wide variety of temperature and/or humidity conditions. Periods of increased temperature (e.g., 50° C. or more) may cause conventional hot-melt adhesives to exhibit an undesirable increase in bond strength when the article is to be used by a consumer. It is believed, without being limited by theory, that at higher temperatures the flowability of the hot-melt adhesive increases enough for it to penetrate further into the pores or capillaries of the substrate. Then, when the adhesive cools, it requires more force to separate the joined surfaces.

While permanent bonds may provide the desired bond strength during a high speed manufacturing process, the increased bond strength and/or infrangibility of the adhesive may be undesirable at other times such as when a consumer attempts to use the article or fastening system and it becomes necessary to break the bond. In order for a disposable absorbent article to be used as intended by a consumer, it may be necessary or desirable to unfold or reposition the fastening system or other portion of the article. The increased bond strength and/or infrangible bond provided by a permanent bonding agent may result in an undesirably difficult unfolding or repositioning experience. In addition, mechanical fastening systems are typically configured to be refastenable (i.e., the fastener can be fastened and unfastened more than once without substantial loss of fastening capability). Applying a permanent bonding agent to the mechanical fastener may undesirably reduce the refastenability of the mechanical fastener, for example, by covering up the engageable portions of the mechanical fastener.

One way to address the high bond strength problems described above may be to use a temporary bonding agent such as a temporary strength adhesive to maintain the fastening system in a folded configuration. Temporary strength adhesives, sometimes referred to as "fugitive" adhesives, are known (see, e.g., U.S. Publication No. 2006/0027320, filed by Kueppers, et al., on Jun. 20, 2005). However, fugitive adhesives are typically used to create temporary, frangible paper-to-paper bonds, for example, for joining cardboard containers and/or portions thereof to one another or for use with envelopes, labels, and the like. Typically, when the bond provided by a fugitive adhesive is broken, the adhesive is no longer tacky and does not readily adhere to anything. Fugitive adhesives are not known in the art for use in the fastening system of an absorbent article such as a disposable diaper. One reason for this may be the difference in materials used in absorbent articles (which typically include at least some polymeric materials as opposed to only paper). Another reason may be that the fastening system for an absorbent article is generally intended to provide a permanent bond or, in the case of a refastenable fastening system, a quasi-permanent bond to maintain the article in the desired position and/or configuration on a wearer. In other words, one goal of the fastening system is to provide sufficient bond strength to prevent the article from undesirably coming unfastened during the intended use of the article, and a temporary bonding agent will typically not help achieve this goal.

In addition, known fugitive adhesives may not form a strong enough initial bond to make them capable of temporarily holding folded portions of absorbent articles in place during a high speed manufacturing process where the folded portions of the absorbent articles could come in to contact with other objects in the manufacturing process. Water-based fugitive adhesives, which are typically used in labeling and envelope applications, have relatively low bond strengths when wet (i.e., when applied). This may be sufficient for use in bonding paper to paper, but it is generally not sufficient for the absorbent article applications described herein. Further, in order for conventional fugitive adhesives to lose strength, they may require active heating, radiation, or the like to reduce their strength, all of which are impractical for use with absorbent articles. Other known fugitive adhesives are solvent cross-linked materials, which may not be suitable for use in the absorbent articles described herein.

Accordingly, it would be desirable to provide a disposable absorbent article comprising a frangible bonding agent for maintaining the article in a particular configuration during a high speed manufacturing process. It would also be desirable to provide a fastening system that is relatively easy to open by a consumer. It would further be desirable to provide a fastening system comprising a frangible bonding agent, which does not impair the fastenability or refastenability of a fastening system.

SUMMARY OF THE INVENTION

In order to provide a solution to the problems set forth above, at least one embodiment described herein provides a disposable absorbent article comprising a fastening system. The fastening system includes first and second opposing surfaces, a web, and at least one engaging member joined to the web. The mechanical fastening system also includes a frangible bonding agent disposed on a first portion of the first surface of the mechanical fastening system.

DETAILED DESCRIPTION OF THE INVENTION

Definitions

Figure 1:
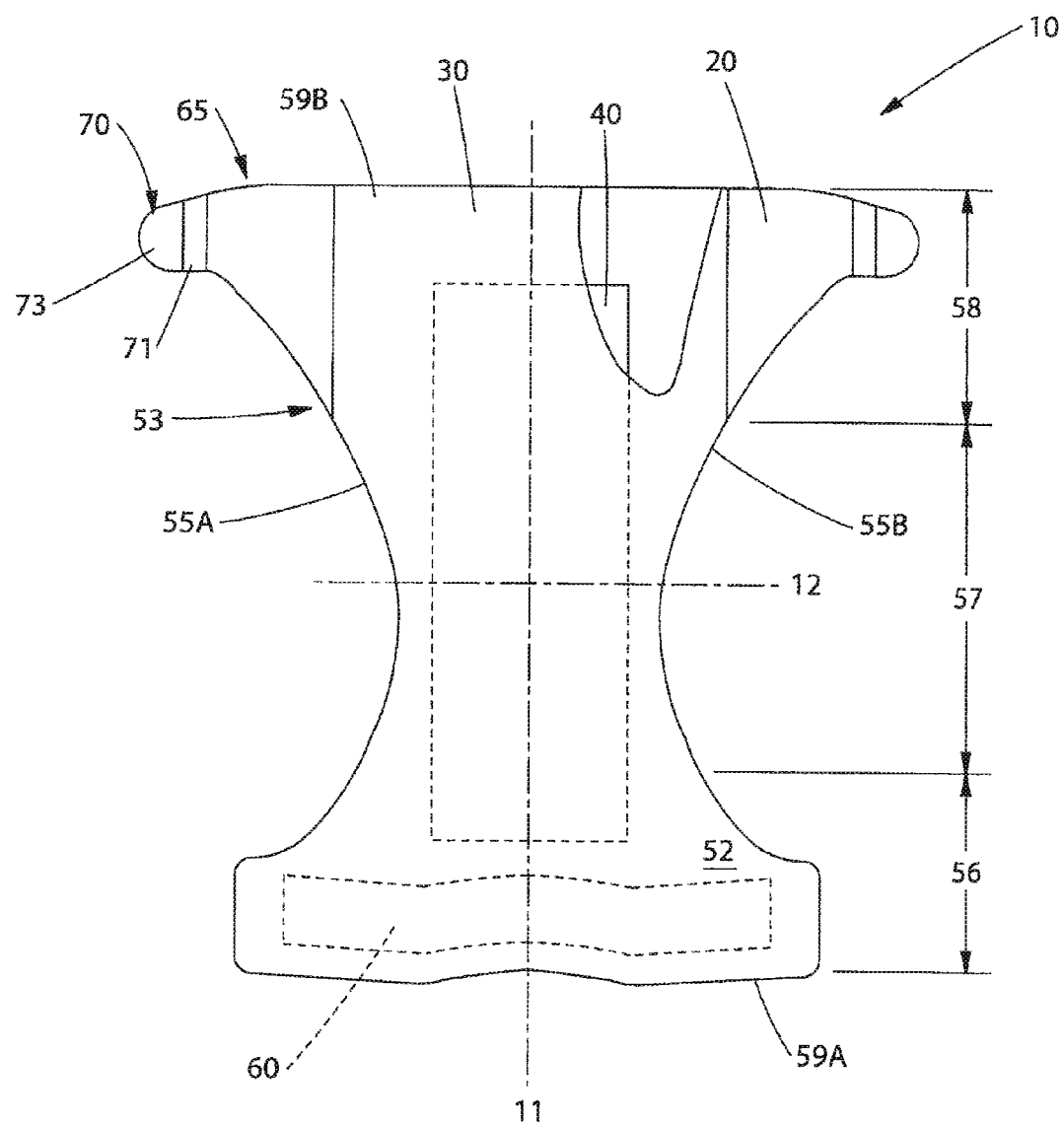
FIG. 1 is a partial cut-away view of a disposable absorbent article.

"Absorbent article" means an article that absorbs and/or contains liquid. Wearable articles are articles placed against or in proximity to the body of a wearer. Wearable absorbent article are absorbent articles placed against or in proximity to the body of a wearer to absorb and contain various exudates discharged from the body. Nonlimiting examples of wearable absorbent articles include diapers, pant-like or pull-on diapers, training pants, sanitary napkins, tampons, panty liners, incontinence devices, and the like.

"Comprising" means that the various components, ingredients, or steps, can be conjointly employed in practicing the disclosed fastening system. Accordingly, the term "comprising" encompasses the more restrictive terms "consisting essentially of" and "consisting of."

"Disposable" means absorbent articles which generally are not intended to be laundered or otherwise restored or reused as an absorbent article (i.e., they are intended to be discarded after a single use and, preferably, to be recycled, composted or otherwise disposed of in an environmentally compatible manner).

"Disposed" means the placement of one element of an article relative to another element of an article. For example, the elements may be formed (joined and positioned) in a particular place or position as a unitary structure with other elements of an article or as a separate element joined to another element of the article. When one element is disposed on another element, the elements or portions thereof may be in direct contact with one another, or the elements or portions thereof may be separated, for example, by the joining means (e.g., adhesive).

"Elastic" means the property of a material or component (e.g., film, fiber, nonwoven, strand, laminate or combinations of these) to elongate, without rupture or breakage, by at least 50% at a load of between 0.1 and 10 N/cm in the Hysteresis Test described in detail in copending U.S. application Ser. No. 12/398,615. Further, upon release of the load, the elastic material or component has set less than or equal to 20% as measured according to the aforementioned Hysteresis Test. For example, an elastic material that has an initial length of 25 mm can elongate to at least 37.5 mm (50% elongation) and, upon removal of the force, retract to a length of 27.5 mm, i.e., have a set of 2.5 mm (10% set). It is to be understood, however, that this definition of elastic does not apply to materials such as individual elastic strands that do not have the proper dimensions (e.g., not wide enough) to be properly subjected to the hysteresis test. Instead, such material is considered to be elastic if it can elongate to at least 50% upon application of a biasing force, and return substantially to its original length (i.e., exhibit less than 20% set) upon release of the biasing force.

"Engage" and variations thereof mean to join two or more elements to one another in a cooperative fashion. For example, a hook/loop type mechanical fastening system may be engaged by entangling the hooks and loops with one another. In another example, two substrates may be engaged by applying an adhesive to one or both substrates and contacting them with one another. In yet another example, a hook/loop type mechanical fastening system may be engaged by applying an adhesive to the hooks of the fastening system and contacting the adhesive with another element, which may or may not include loops, such that the hook containing portion of the fastening system and the contacted substrate are joined to one another due, at least partially, to the adhesive.

"Extensible" material is material that elongates, without rupture or breakage, by at least 50% at a load of between 0.1 and 10 N/cm in the Hysteresis Test. Further, upon release of the load, the material has set greater than 20% as measured according to the aforementioned Hysteresis Test. For example, an extensible material that has an initial length of 25 mm can elongate at least to 37.5 mm (50% elongation) and, upon removal of the applied force, retract to a length of 35 mm, i.e., have a set of 10 mm (40% set), when subjected to the aforementioned Hysteresis Test.

"Film" means a substantially nonporous material made by a process that includes extrusion of, e.g., a polymeric material through a relatively narrow slot of a die. A film may be impervious to a liquid and pervious to an air vapor, but need not necessarily be so.

"Foldable" means that a component can be bent such that one portion of the component can be placed over another portion of the same component in an overlaying relationship without permanently altering its ability to function as intended.

"Frangible Bond" means a bond that through deformation tends to break up into fragments relatively easily via cohesive failure, rather than deforming plastically and retaining its cohesion as a single object. Frangible bonds are sometimes referred to as being brittle.

"Garment-facing side" means the outermost portion of an element of a wearable absorbent article when the absorbent article is worn as intended. The opposing side, or innermost portion, of the same element is referred to as the "wearer-facing side." It is to be understood that the garment-facing side and the wearer-facing side of an element are relative to the wearer of the article with the garment-facing side being furthest from the wearer and the wearer-facing side being closest to the wearer. In the example of a typical disposable diaper, the portion of the outer cover that faces away from the wearer is the garment-facing side while the opposing side of the outer cover is the wearer-facing side.

"Joined" means configurations whereby an element is directly secured to another element by affixing the element directly to the other element (e.g., ultrasonic bonding, thermal bonding, high pressure bonding and the like), and configurations whereby an element is indirectly secured to another element by affixing the element to intermediate member(s) that in turn are affixed to the other element (e.g., adhesive bonding where the adhesive is the intermediate member).

"Laminate" means two or more materials that are bonded to one another by methods known in the art (e.g., adhesive bonding, thermal bonding, ultrasonic bonding, or high pressure bonding using non-heated or heated patterned roll).

"Longitudinal" means a direction running substantially perpendicular from a waist end edge to an opposing waist end edge of an absorbent article when the article is in a flat out, uncontracted state, or from a waist end edge to the bottom of the crotch in a bifolded article. Directions within 45 degrees of the longitudinal direction are considered to be "longitudinal." "Lateral" refers to a direction running from a side edge to an opposing side edge of an article and generally perpendicular to the longitudinal direction. Directions within 45 degrees of the lateral direction are considered lateral.

"Machine direction" ("MD") is the direction parallel to the direction of travel of the web in a manufacturing process. Directions within 45 degrees of the MD are considered to be machine directional. The "cross machine direction" ("CD") is the direction substantially perpendicular to the MD and in the plane generally defined by the web. Directions within 45 degrees of the CD are considered to be cross directional.

"Nonwoven" means a porous, fibrous material made from continuous (long) filaments (fibers) and/or discontinuous (short) filaments (fibers) by processes such as spunbonding, meltblowing, carding, and the like. Nonwovens do not have a woven or knitted filament pattern. Nonwovens may be liquid permeable or impermeable.

"Outboard" and "inboard" mean, respectively, the location of an element disposed relatively far from or near to the longitudinal centerline of an absorbent article with respect to a second element. For example, if element A is outboard of element B, then element A is farther from the longitudinal centerline than is element B. Similarly, "outward" and "inward" mean, respectively, directions which are away from or toward the longitudinal centerline.

"Refastenable" means the ability of two or more elements or portions of elements, which are fastened together, to be unfastened and refastened without substantial degradation of fastener performance or damage to surrounding components of the article that would impair the article's continued use. It will be appreciated that a refastenable component need not have an infinite life span, but it is sufficient that the components attached in a refastenable manner can be separated and re-attached successively several times over the typical use life span of the article. It will also be appreciated that the aggressiveness of actual fastening may be reduced significantly from fastening to refastening in absolute terms, but that such reduction is not "substantial degradation" of fastener performance if the resulting refastened strength is sufficient for the fastening system's purpose of use.

"Web" means a material capable of being wound into a roll. Webs may be films, nonwovens, laminates, apertured laminates, and the like.

"X-Y plane" means the plane defined by the MD and CD of a moving web or the length and width of a piece of material.

While some embodiments described herein may refer to a disposable diaper, it is to be understood that the fastening system disclosed herein is not limited to such embodiments, but may in fact be practiced to great advantage with any suitable absorbent article.

Disposable Absorbent Article

FIG. 1 shows a partial cut-away, plan view of a diaper 10 in a flat-out, uncontracted state (i.e., with no elastic induced contraction). Portions of FIG. 1 are cut away to more clearly show the construction of the diaper 10. The outer, garment-facing surface 52 of the diaper 10 is oriented towards the viewer and the opposing inner, wearer-facing surface is oriented away from the viewer. As shown in FIG. 1, the diaper 10 may include a liquid pervious topsheet 20; a liquid impervious outer cover 30 joined with at least a portion of the topsheet 20, for example, along the periphery 53 of the diaper 10; and an absorbent core assembly 40 positioned between the topsheet 20 and the outer cover 30. The diaper 10 may include an elastic waist feature 60 and a fastening system. The fastening system may include an ear 65 joined to at least one waist region 56 and/or 58. In certain embodiments, the ear 65 and one or both waist regions 56 and/or 58 may be formed from as a unitary structure, for example, by forming the two elements from the same substrate. The ear 65 may include a fastening tab 70, which extends laterally outwardly from the diaper 10 and an engaging member 71 disposed on the fastening tab 70. The engaging member 71 may be engageable with another portion of the diaper 10 (e.g., another portion of the ear 65 and/or a receiving member). "Engageable" means one element is configured to be joined to another element, for example, through the creation of an entanglement-type mechanical bond. The fastening tab 70 may include a gripping portion 73 that enables a user to grasp and/or manipulate the fastening tab 70. The gripping portion 73 may extend laterally outwardly from the edge of the engaging member 71 at a distance of greater than 0 mm, for example between 0 and 20 mm. The diaper 10 may also include a first waist region 56, a second waist region 58, a crotch region 57 disposed between the first and second waist regions 56 and 58, and a periphery 53, defined by opposing longitudinal side edges 55A and 55B and opposing end edges 59A and 59B. The inner, wearer-facing surface of the diaper 10 may include at least a portion of the topsheet 20 and other components, which may be joined to the topsheet 20. The outer, garment-facing surface 52 may include at least a portion of the outer cover 30 and other components, which may be joined to the outer cover 30. The diaper may include a longitudinal centerline 11 and a lateral centerline 12 orthogonal thereto.

The topsheet 20 may be flexible, soft feeling, and non-irritating to the wearer's skin. It may be desirable to configure the topsheet to be liquid pervious (i.e., permitting liquids such as menses, urine, and/or runny feces to readily penetrate through its thickness). For example, the topsheet 20 may be made of a hydrophilic material that promotes rapid transfer of liquids through the topsheet 20. In certain embodiments, the topsheet 20 may be made of a hydrophobic material (e.g., polyolefin nonwoven and/or film), at least a portion of which (e.g., the wearer-facing surface) has been treated to be hydrophilic so that liquids will transfer through the topsheet more rapidly. The topsheet 20 or portions thereof may be rendered more hydrophilic, for example, by treatment with a surfactant. A suitable topsheet 20 may be manufactured from a wide range of materials such as woven and nonwoven materials (e.g., a nonwoven web of fibers); polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

The absorbent core assembly 40 is generally capable of absorbing and retaining liquids (e.g., menses, urine, and/or other bodily exudates). The absorbent core assembly 40 may be compressible, conformable, and non-irritating to the wearer's skin. The configuration and construction of the absorbent core assembly 40 may be varied (e.g., the absorbent core assembly may have varying caliper zones and/or have a profile so as to be thicker in the center; hydrophilic gradients; gradients of the absorbent composite of the present invention, superabsorbent gradients; or lower average density and lower average basis weight zones (e.g., acquisition zones); or may comprise one or more layers or structures). The size and absorbent capacity of the absorbent core assembly 40 may be varied to accommodate different uses such as diapers, incontinence pads, pantiliners, sanitary napkins, and to accommodate wearers ranging from infants to adults. In certain embodiments, the diaper 10 may have an asymmetric, modified T-shaped absorbent core assembly 40 having a narrowing of the side edge 46 in the first waist region 56 but remaining generally rectangular-shaped in the second waist region 58. In certain embodiments, the absorbent core may be arranged in a bucket-type configuration, for example, as described in U.S. Publication No. 2008/0004591, titled "Absorbent Article Having An Anchored Core Assembly," filed by Desai, et al., Jun. 7, 2007. Other suitable examples of absorbent core assemblies are described in U.S. Pat. Nos. 4,610,678; 4,673,402; 4,888,231; and 4,834,735. The absorbent core assembly may further comprise a dual core system containing an acquisition/distribution core of chemically stiffened fibers positioned over an absorbent storage core, as detailed in U.S. Pat. Nos. 5,234,423 and 5,147,345. The absorbent core assembly 40 may include absorbent components that are commonly used in absorbent articles, such as a dusting layer, a wicking or acquisition layer, and/or a secondary topsheet for increasing the wearer's comfort.

As shown in FIG. 1, the outer cover 30 may be configured to substantially cover the entire exterior, garment-facing surface 52 of the diaper 10. The absorbent core assembly 40 may be joined with the topsheet 20, the outer cover 30, or both in any manner known in the art. For example, the outer cover 30 and/or the first topsheet 20 may be secured to the absorbent core assembly 40 or to each other by a uniform continuous layer of adhesive, a patterned layer of adhesive, or an array of separate lines, spirals, or spots of adhesive, heat bonds, pressure bonds, ultrasonic bonds, mechanical bonds, or combinations of these. The outer cover 30 may be manufactured from a thin plastic film, although other flexible liquid impervious materials may also be used. The outer cover 30 may comprise a woven or nonwoven material, polymeric films such as thermoplastic films of polyethylene or polypropylene, or composite materials such as a film-coated nonwoven material or a film-nonwoven laminate. An example of a suitable outer cover 30 is a polyethylene film having a thickness of from about 0.012 mm to about 0.051 mm. Exemplary polyethylene films are manufactured by Clopay Corporation of Cincinnati, Ohio, under the designation P18-1401 and by Tredegar Film Products of Terre Haute, Ind., under the designation XP-39385. In certain embodiments, the outer cover 30 may include two or more layers of material joined together to form a laminate structure. For example, the outer cover 30 may include one or more liquid impervious film layers 31 joined to one or more nonwoven layers 32 in any suitable configuration desired. In certain embodiments, the outer cover 30 may be used to improve the aesthetic and/or textural quality of the exterior surface of the diaper 10. For example, it may be desirable provide an outer cover 30 with an embossed or matte finish that imparts a cloth-like appearance and/or feel to the outer cover 30.

Figure 2:
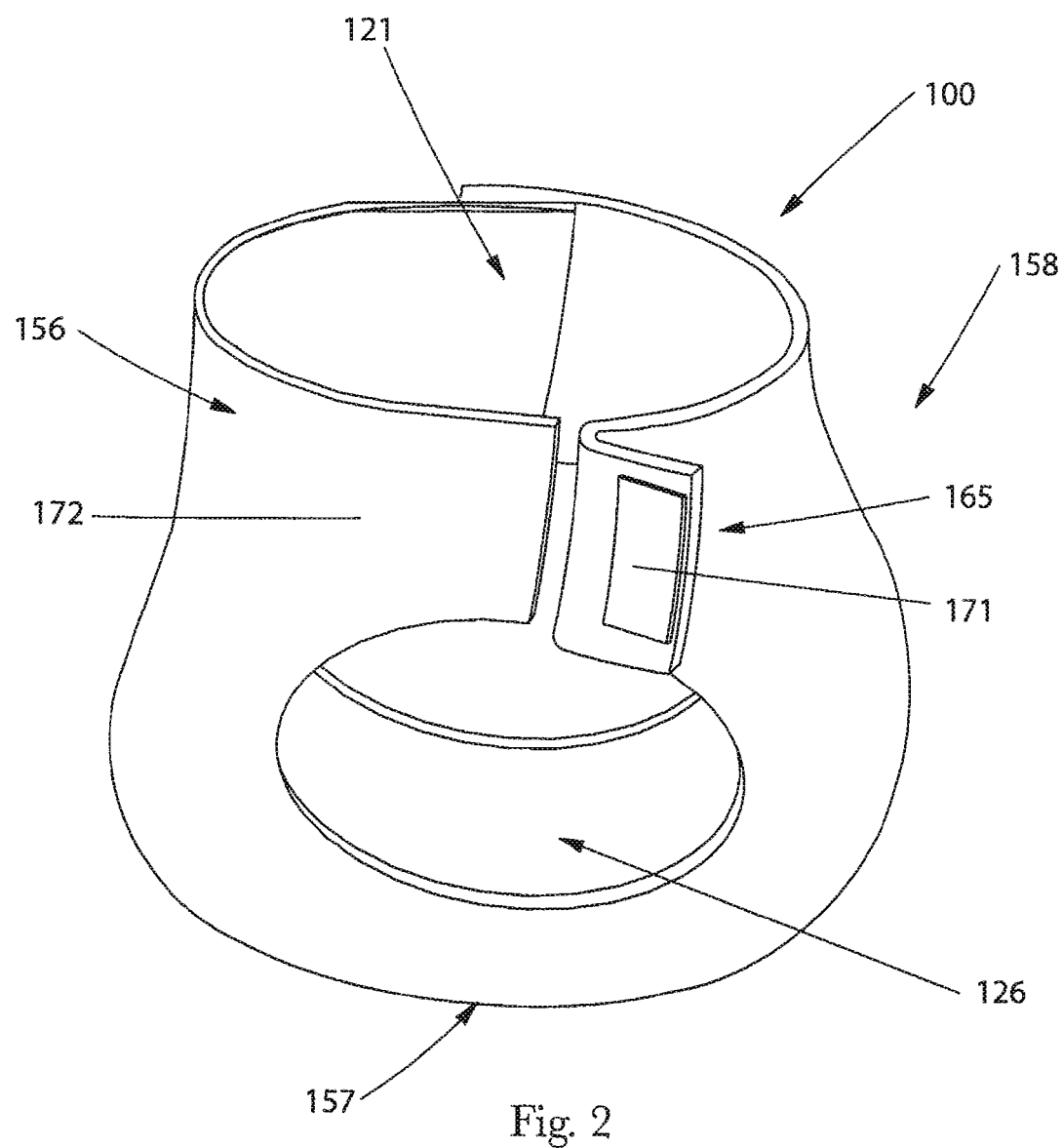
FIG. 2 is a perspective view of a disposable absorbent article.

FIG. 2 shows a diaper 100 in a partially fastened configuration (i.e., one fastener is fastened and the other fastener is not fastened). The front and back waist regions 156 and 158 include portions(s) of the diaper 100 that may be joined to one another (e.g., with fastening system 170) to form a waist opening 121 that encircles the waist of a wearer when the diaper 100 is worn as intended. The diaper 100 may include a discrete ear 165 joined to at least one waist panel 156, 158 by any suitable means known in the art. In certain embodiments, the ear 165 and one or both waist panels 156, 158 may be formed as a unitary element, for example, from a single piece of material. Disposed on the ear 165 may be one or more components that make up the fastening system, such as the engaging member 171, which can be joined to another portion of the diaper 100 such as, for example, a receiving member 172. The receiving member 172 may be disposed on the front waist region 156, the back waist region 158, and/or any other suitable portion of the diaper 100. The engaging member 171 and receiving member 172 may each include a surface feature that complements and is capable of forming a mechanical bond with the surface feature of the other (e.g., hooks and loops or tab and slot). The diaper 100 may include a crotch region 157 extending between the front and back waist regions 156 and 158. The front and back waist regions 156 and 158 may each include one or more elastic waist features. The diaper 100 may include one or more leg openings 126 defined by a leg band region. The leg opening 126 may have a minimum hoop diameter of at least 4 cm and/or a maximum hoop diameter of at least 10 cm. The leg opening 126 may be configured to have a range of hoop diameters whereby the maximum hoop diameter is at least 3×, 5× or even 10× greater than the minimum hoop diameter.

In certain embodiments, a diaper or similar disposable absorbent article may be preformed by the manufacturer to create a pant or pant-like article. A pant may be preformed by any suitable technique including, but not limited to, joining together portions of the article using refastenable and/or non-refastenable bonds (e.g., seam, weld, adhesive, cohesive bond, fastener, etc.). For example, the diaper 10 of FIG. 1 may be manufactured with the engaging member 71 permanently or temporarily engaged to a receiving member or other suitable portion of the diaper to form an article in a fastened configuration or partially fastened configuration. In certain embodiments, an absorbent article such as the diaper 10 of FIG. 1 may be manufactured with one or more front ears joined to one or more back ears by way of a bond such as an adhesive bond, a mechanical bond, or any other suitable bonding technique known in the art. Suitable pants are disclosed in U.S. Pat. Nos. 5,246,433; 5,569,234; 6,120,487; 6,120,489; 4,940,464; 5,092,861; 5,897,545; and 5,957,908.

Fastening System

Suitable fastening systems for use herein may include commonly known mechanical fastening systems (i.e., fastening systems that form mechanical bonds between themselves and/or another component when fastened, as opposed to, for example, the chemical bond typically formed by an adhesive fastening system). A particularly suitable mechanical fastening system is a hook/loop type mechanical fastening system. Another suitable mechanical fastening system is a tab/slot type mechanical fastening system. Other examples of mechanical fastening systems include, without limitation, hermaphroditic, friction, static, magnetic, button/button hole, zippers, buckles and the like. Examples of mechanical fastening systems and configurations of mechanical fastening systems may be found in U.S. Pat. Nos. 4,662,875; 4,846,815; 4,894,060; and 6,432,098; and PCT Publication No. WO92/022273.

A mechanical fastening system such as a hook/loop type fastening system typically includes an engaging member comprising engaging element(s) (e.g., hooks and the like) and a receiving member comprising complementary receiving element(s) (e.g., loops and the like). The engaging elements operatively engage with the complementary receiving elements (e.g., by becoming entangled) to form a mechanical bond. In certain embodiments, the engaging member may comprise a base. The base may provide a relatively strong backing on and/or into which are imbedded, bonded, woven or fused the engaging elements. In certain embodiments, the engaging elements and the base may be formed from the same material as a unitary element. The base or portions thereof may be flexible or stiff, as desired. The base may be manufactured from a wide variety of materials commonly used for backings for mechanical fasteners (e.g., nylon, polypropylene, polyethylene, or any equivalent material or blends of these materials). In certain embodiments, the base may comprise a woven nylon material secured to a nonwoven or a film member by an adhesive and/or other commonly known bonding means. The base may have an engaging side and a non-engaging side opposed thereto. The non-engaging side of the base may be permanently joined to a fastening tab or another component of the absorbent article, such as a waist panel, side panel, or ear. The engaging elements may project out of the engaging side of the base, and each engaging element may have a proximal end joined to the engaging side of the base and a distal end spaced away from the proximal end. The distal and proximal ends of the engaging element may be connected with a stem that extends between the two ends. The shape of the engaging elements may be selected to provide a suitable amount of entanglement with complementary receiving elements. Nonlimiting examples of suitable engaging element shapes include hook-shaped, mushroom-shaped, and t-shaped. Suitable examples of engaging element material include commercially available hook material from Aplix, sold under the product codes 963, 960, 957, and 942, and 3M, sold under the product codes CS200, CS300, CS600, or MC6.

In certain embodiments, the receiving member may include commercially available loop material (e.g., product code #18904 available from Guilford, Wilmington N.C.; or product code KLT available from 3M). In certain embodiments, the receiving member may simply be a nonwoven web (e.g., a single layer of nonwoven or a laminate with at least one nonwoven surface or surface portion). Nonwovens are typically formed from a multitude of fibers arranged in a substantially random pattern. This random arrangement of fibers may provide sufficient loop formations or other similar features on the surface of the nonwoven for desirably engaging with the engaging elements of an engaging member. Typical hook/loop type mechanical fastening systems may exhibit Shear values of greater than 10N, as measured according to the Shear Test, when the fastening system is fastened in contemplation of the intended use of the article (e.g., to hold a diaper around the waist of wearer). Suitable examples of mechanical fastening system elements are disclosed in U.S. Pat. Nos. 5,032,122 and 5,326,612; and PCT Publication Nos. WO07/096,841, WO07/096,842, WO96/022065, WO96/004812.

The fastening system may include a fastening tab (e.g., disposed on an ear or side panel). In certain embodiments, the fastening tab may be formed from the same or different material as the ear or side panel to which it is joined. The fastening tab may be formed as a laminate, for example, by joining two or more layers of nonwoven and/or film material to one another in a face-to-face relationship. Nonlimiting examples of suitable nonwoven and film materials include polymers, copolymers, and/or blends of natural and/or synthetic materials (e.g., cotton; cellulose; rayon; polyolefin such as polypropylene and polyethylene; polyester; and nylon). Fibers used herein may be monocomponent or bicomponent fibers (e.g., core/sheath, island, or side-by-side configurations), and may be any shape (e.g., round, flat, trilobal, or crimped). It is to be understood that any material or fiber shape known to be suitable for making the films, nonwovens, and/or engaging elements of an absorbent article fastening system may also be suitable for use herein. The layers of the laminate may be joined to one another and/or the engaging member by any suitable means known in the art (e.g., adhesive, ultrasonic, thermal and/or high pressure bonding). In certain embodiments, the fastening tab may be formed from one or more materials that have been subjected to an activation process (e.g., incremental stretching of a material resulting in permanent mechanical deformation). It may be desirable to provide a foldable fastening system, for example, by forming the fastening tab from pliable materials. In a foldable fastening system, the ear and/or the fastening tab may be folded over and joined to themselves, one another, and/or another article component by contacting an engageable portion of the ear or fastening tab (e.g., engaging elements or an adhesive containing portion) with a complementary portion of the ear, fastening tab, and/or other article component (e.g., a nonwoven or film surface portion proximate to the engaging member or a receiving member or portion thereof). In one example, the fastening tab and/or the ear to which the fastening tab is joined may be formed as a four layer laminate that includes a layer of 65 micron film sandwiched between a layer of 27 grams per square meter ("gsm") carded nonwoven and a layer of 17 gsm SMS (i.e., spunbond-meltblown-spunbond) nonwoven, and a 40 gsm spunbond nonwoven layer joined to the 27 gsm nonwoven layer. In this example, an engaging member in the form of hook material may be permanently bonded to the laminate (e.g., with an adhesive). The fastening tab and/or ear to which it is joined may have any suitable shape desired, such as rounded edges, squared edges, and/or a combination of these. The fastening tab and the ear (and/or other article components) may be formed as a unitary element. However, in certain embodiments, a discrete fastening tab may be attached directly to the side panel (and/or other component) of an article. Nonlimiting examples of suitable fastening tab and ear shapes and configurations are disclosed in PCT Publications Nos. WO07/072,421; WO07/072,386; and WO07/069,227; and U.S. Pat. No. 7,416,545.

Figure 3:
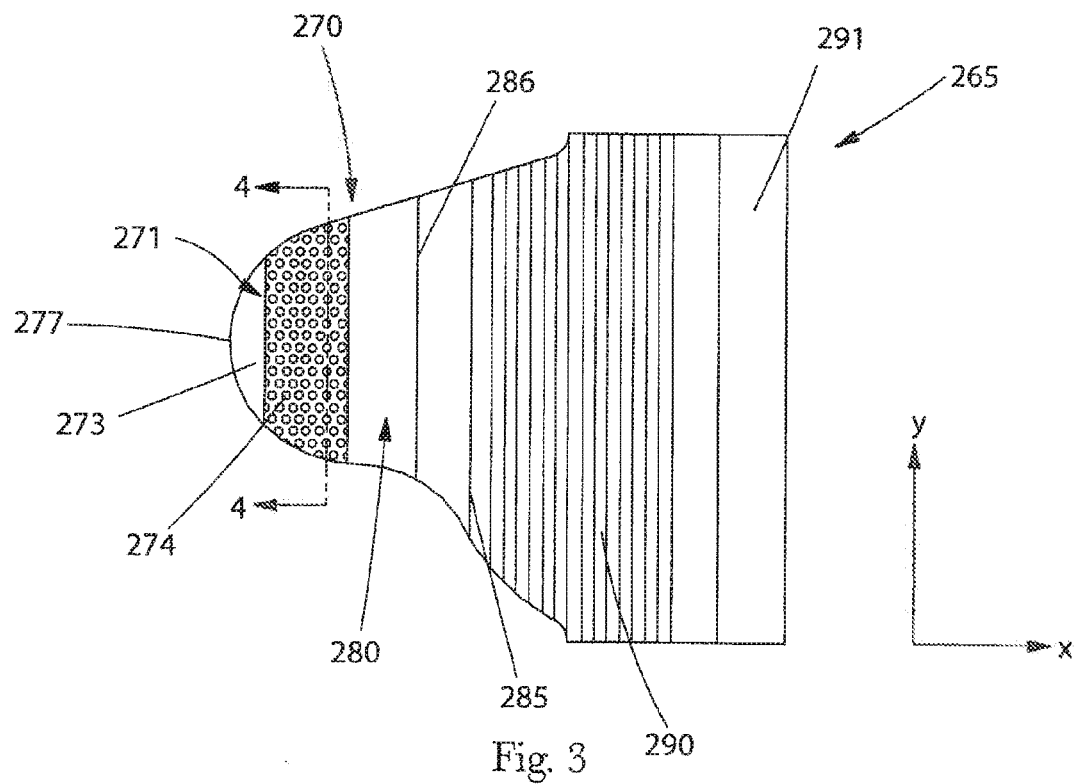
FIG. 3 is a plan view of an ear and a fastening tab.

FIG. 3 shows a plan view of an ear 265. The ear 265 may include a fastening tab 270 that extends laterally outwardly from the ear 265. The fastening tab 270 may include an engaging member 271 and a gripping portion 273. The engaging member 271 may include a plurality of engaging elements 274. The gripping portion 273 generally extends outwardly from the engaging member 271 in the x-direction and defines the outer edge 277 of the fastening tab 270. The ear 265 may include a support member 280 that supports one or more other elements of the ear 265 and/or fastening tab 270 (e.g., the engaging member 271). The support member 280 may be formed from films, woven materials, nonwoven materials, extruded or sprayed polymeric materials, combinations of these and the like. The support member 280 may be configured to engage with the engaging member 271 and/or a frangible bonding agent such as a suitable fugitive adhesive. For example, the support member 280 may be configured to include a nonwoven or film material as the outer layer of an extensible or elastic multilayer laminate structure. In an alternative example, the support member 280 may be formed as a single layer of extensible or elastic nonwoven or film material. The ear 265 may include an attachment edge 291 where the ear 265 may be joined to an article or article component (e.g., a side panel or absorbent article chassis). The engaging elements 274 are typically engageable with another portion of the ear 265 (e.g., support member 280 or the corrugations 290 formed in the support member 280) and/or a receiving member disposed elsewhere on the article. In certain embodiments, the fastening tab 270 and/or the ear 265 may be folded over itself (e.g., along first folding line 285, second folding line 286, or any other portion of the fastening tab 270 or ear 265, as desired) such that the engaging elements 274 contact the support member 280. The engaging elements 274 may extend from edge to edge of the fastening tab 270 in the y-direction, but need not necessarily do so. In certain embodiments, the fastening tab 270 may be elastic. That is, the fastening tab 270 may be stretched beyond its original length by a tensile force and when the tensile force is removed the fastening tab 270 exhibits less than 20% set (i.e., exhibits at least 80% recovery). The elasticity of the fastening tab 270 may be provided by a plurality of corrugations 290 formed in the support member 280, for example, by a commonly known incremental stretching process ("activation"). Additionally or alternatively, an extensible nonwoven may be joined with an elastic material such as one or more elastic strands and/or an elastic film or nonwoven material. The nonwoven may be joined to an unstrained (i.e., relaxed) elastic material before, during, or after an activation process to form a so-called zero-strain stretch laminate, or joined to a strained (i.e., stretched) elastic material to form a so-called live-stretch laminate.

Figure 3A:
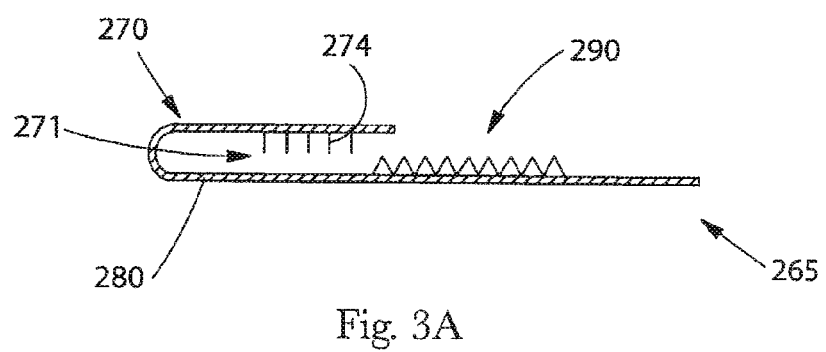
FIG. 3A is schematic cross-section view of a folded fastening tab.

FIG. 3A shows a schematic cross-section view of an example of the ear 265 and fastening tab 270 of FIG. 3 in a folded configuration. As shown in FIG. 3A, the fastening tab 270 is folded over itself in the x-direction along folding line 286. The entire engaging member 271 or a substantial portion thereof (e.g., a majority of the engaging elements 274) may contact the corrugated portion 290 of the ear 265 in an overlaying configuration. In certain embodiments, however, it is contemplated that no portion of the engaging member 271 or only a relative few of the engaging elements 274 may contact the corrugated portion 290 in an overlaying configuration. The fastening tab 270 and/or ear 265 may be folded in any suitable configuration desired. For example, the fastening tab 270 and/or ear 265 may be folded more than once in the same or different direction(s) (e.g., inwardly and/or outwardly). In certain embodiments, the fastening tab 270 may be folded such that a portion of the fastening tab 270 still extends past the longitudinal side edge of the article of which it is a part.

Figure 4A:
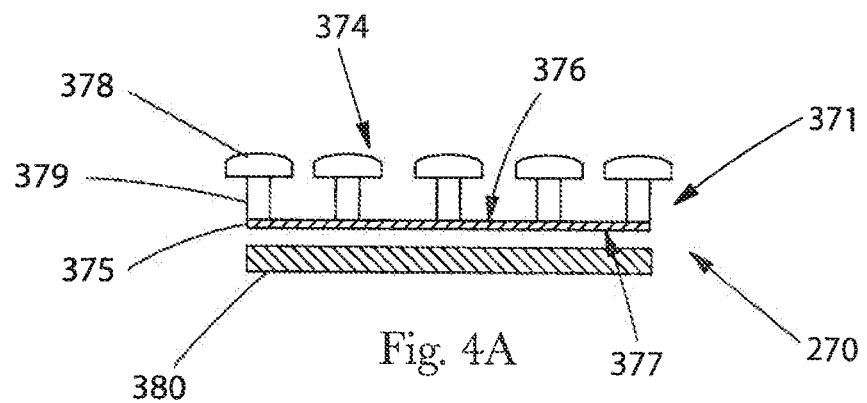
FIGS. 4A-4C are schematic cross-section views of examples of the fastening tab of FIG. 3 along line 4-4.

FIG. 4A shows a schematic cross-section view of an example of the fastening tab 270 along line 4-4. The fastening tab 270 includes an engaging member 371 joined to a support member 380. As shown in this example, the engaging member 371 and the support member 380 may be coterminous, but need not necessarily be so. The engaging member 371 may include a base 375 and a plurality of engaging elements 374. Each of the engaging elements 374 may have a stem 379 joined at one end to the engaging side 376 of the base 380 and an enlarged head 378 positioned at the end of the stem 379 opposite the base 380. In certain embodiments, the engaging elements 374 may include a head 378 joined to the base 380 with substantially no intervening stem 379. The head 378 of the engaging element 374 may have a smooth, generally convex top surface for providing a relatively skin-friendly surface should the skin of the wearer come in contact with the engaging elements 374, and a bottom surface extending radially outward from the stem 379 for engaging the fibers of the nonwoven member 380 and/or a receiving member. The shape of the engaging elements 374 in FIG. 4A is sometimes referred to as "mushroom shaped." The non-engaging side 377 of the base may be joined to the support member 380 with an adhesive or any other suitable bonding means known in the art. However, it may be desirable to select a bonding means which minimizes damage to the engaging elements.

Figure 4B:
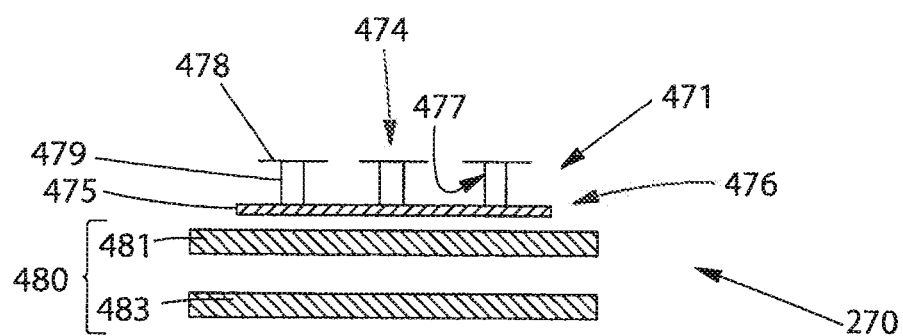

FIG. 4B shows a schematic cross-section view of an example of the fastening tab 270 along line 4-4. The fastening tab 270 includes an engaging member 471 and a support member 480. The support member 480 may be formed as a laminate comprising an upper nonwoven layer 481 and a lower nonwoven layer 483. The engaging member 471 includes a base 475 joined to the upper nonwoven layer 481 of the support member 480 and a plurality of engaging elements 474 projecting out from the base 475. The engaging elements 474 may include a stem 479 joined at the proximal end 476 to the base 475 and a substantially flat head 478 positioned at the distal end 477 of the stem 479. The shape of the engaging elements 474 in FIG. 4B is sometimes referred to as "T-shaped." As shown in this example, the engaging member 471 and the support member 480 are not coterminous.

Figure 4C:
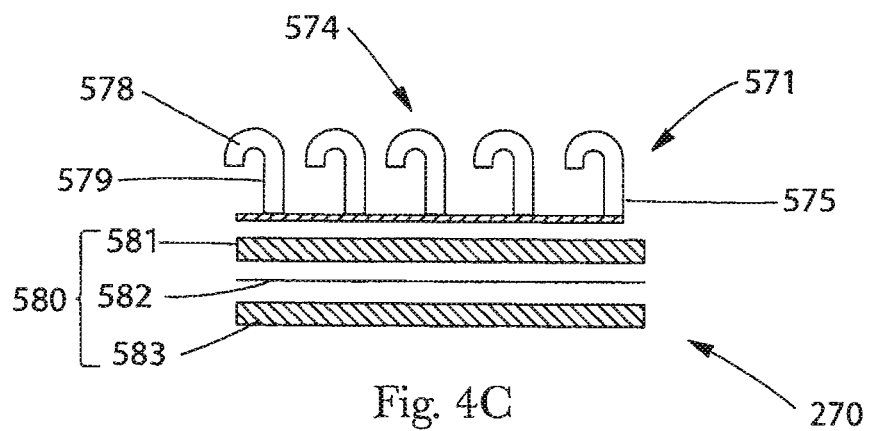

FIG. 4C shows a schematic cross-section view of an example of the fastening tab 270 along line 4-4. The fastening tab 270 includes an engaging member 571 and a support member 580. The support member 580 may be configured as a multilayer laminate that includes an elastic layer 582 sandwiched between upper and lower non-elastic layers 581 and 583, respectively. In certain embodiments, one or more layers 581, 582, and 583 of the laminate may also be configured as a multilayer structure comprising more than one layer of the same or different material. The elastic layer 582 may include elastic strands, elastic films, and/or elastic nonwovens, as desired. The non-elastic layers may include activated or non-activated films and/or nonwovens. The engaging member 571 may include a base 575 joined to the upper nonwoven layer 581 of the support member 580 and a plurality of engaging elements 575 projecting out from the base 575. The engaging elements 574 may include a stem 579 joined at one end to the base 575 and a curved head 578 positioned at the end of the stem 579 opposite the base 575. The shape of the engaging elements 574 in FIG. 4C is sometimes referred to as "hook-shaped."

In certain embodiments, the mechanical fastening system may be configured as a slot/tab type fastening system. Slot/tab type mechanical fastening systems generally include one or more first fastening members in the form of a tab and one or more second fastening members in the form of a slot. The tab may be an elongated member having a length and, in certain embodiments, a grip portion generally adjacent to and extending outwardly from the tab. The grip portion may help a user grip the tab when fastening or unfastening the fastening system. The tab may be of any size and/or shape. Generally, the tab is sized to fit through the slot with little or no bending or deformation of either component. The tab may be made from any suitable material including without limitation plastics, films, foams, nonwoven webs, woven webs, paper, laminates, steel, fiber reinforced plastics and the like, or combinations thereof. In embodiments where the fastening system is used near or against the skin of a wearer, it is preferred that the materials making up the tab be flexible. The flexibility allows the fastening device to conform to the shape of the body and thus, reduces the likelihood that the fastening device will irritate or injure a wearer's skin. The slot is that portion of the fastening device through which the tab is passed in order to engage the fastening system. The slot is typically sized such that the tab may easily pass through the slot without undue bending or deformation of either component. The slot may include a grip portion that extends laterally outwardly from the slot. The slot may be made from any suitable material which is generally considered to be skin friendly. The slot and/or tab may be unitary with the article to which it is attached or may be a separate element(s) joined thereto. The slot and/or tab may be joined to the article at any suitable location. In a disposable absorbent article, the slot and/or tab may be an extension of the material making up a side panel of the article. In such cases, it may be desirable to provide additional material or to process the material of the side panel so as to provide the side panel with physical properties suitable for use as a slot and/or tab. In a simple form, the fastening system may be engaged by passing the tab partially or completely through the slot. Once the tab has been passed through the slot, one or more components of the tab may, individually or in cooperation with one or more other fastening system elements, prevent the tab from slipping back through the slot and disengaging the fastening system. Examples of slot/tab type fastening systems are described in PCT Publication Nos. WO07/036,908; WO03/105740, WO99/11211 and WO99/11212 filed by Kline, et al.

Figure 8:
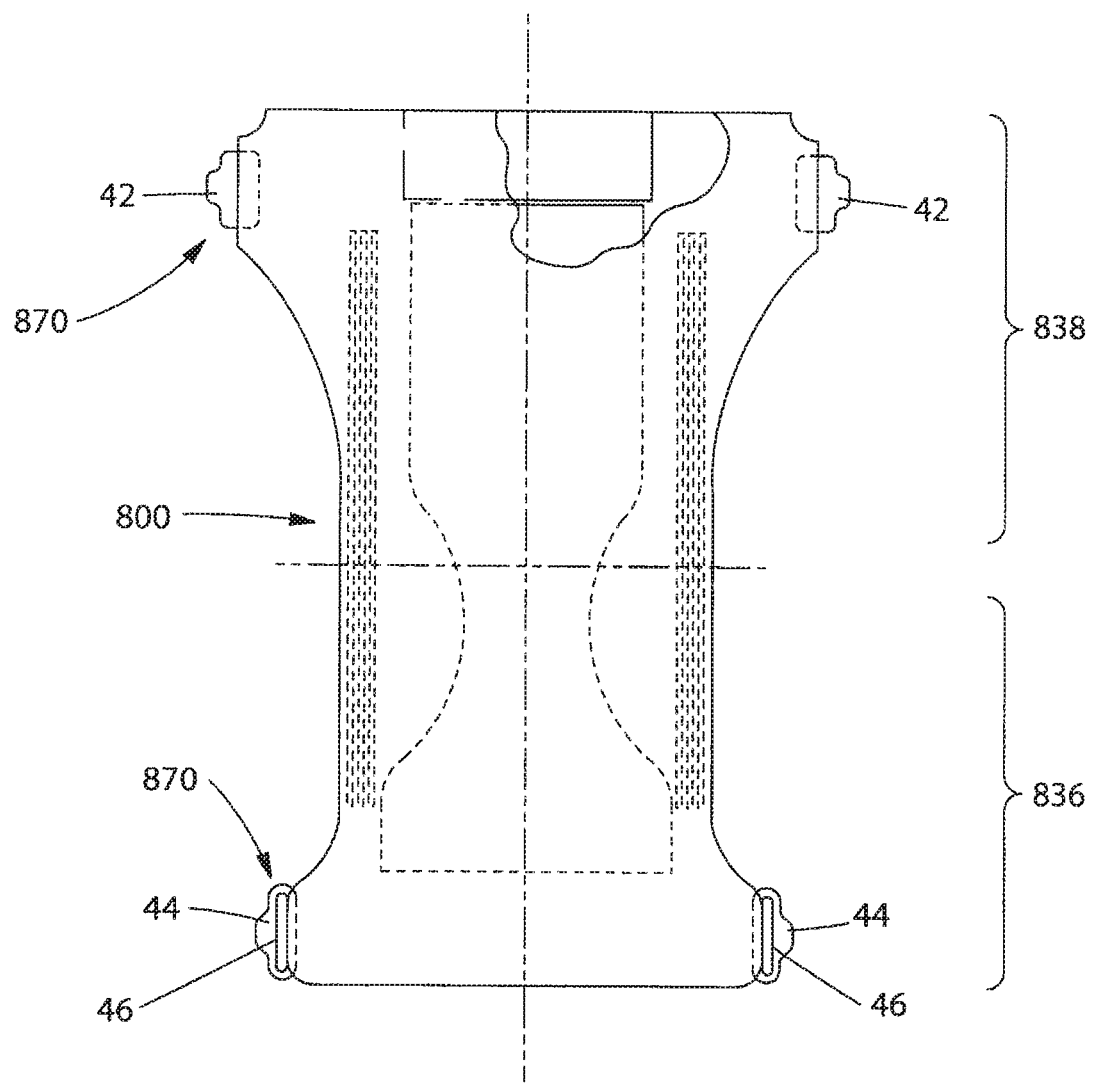
FIG. 8 is a plan view of a disposable absorbent article.
Figure 9:
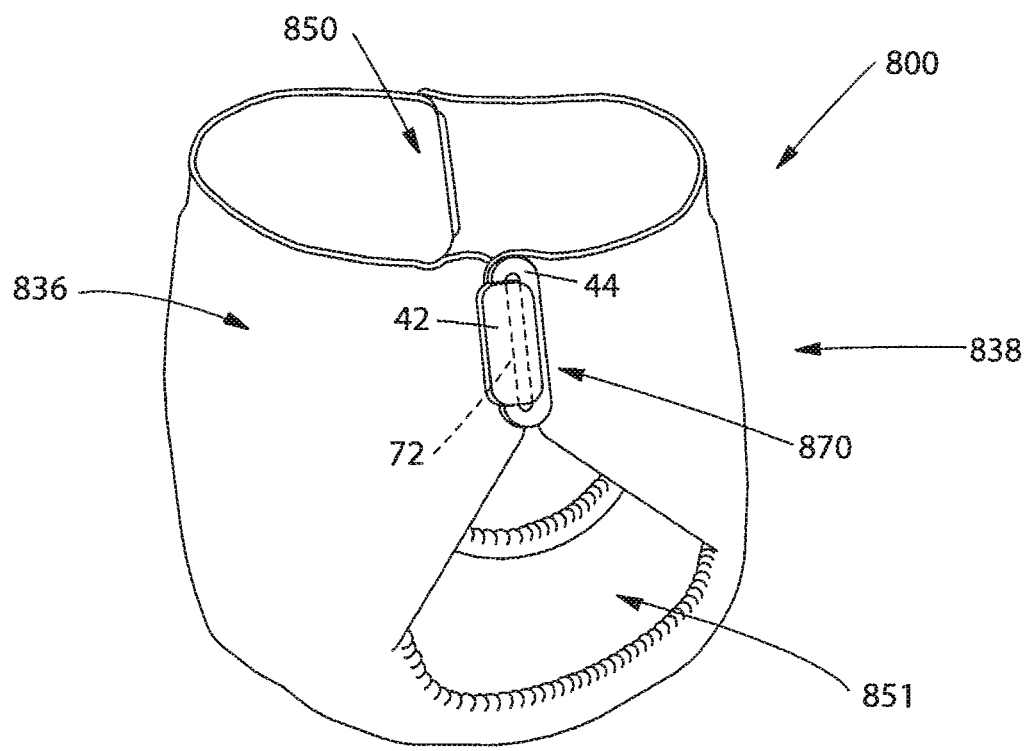
FIG. 9 is a perspective view of disposable absorbent article.

FIG. 8 shows a partial cut-away, plan view of a disposable absorbent article 800 in a flat-out, uncontracted state (i.e., with no elastic induced contraction). The article 800 may include a slot/tab type mechanical fastening system 870. The fastening system 870 may include one or more tab members 42 and one or more slot members 44. The slot members 44 may each have one or more slots 46 configured to pass at least a portion of the tab member 42 there through. FIG. 9 shows the disposable absorbent article 800 of FIG. 8 in a fastened configuration (i.e., the fastening system 870 is engaged). As shown in FIG. 9, at least one of the tab members 42 is passed through a slot 46 of at least one of the slot members 44, to join the front waist portion 836 and the rear waist portion 838 of the article 800 to one another to form a waist opening 850 and at least one leg opening 851. The tab members 42 may be joined to the article 800 or a component thereof (e.g., side panel) along a line of attachment 72. The tab member 42 may include a retaining element that helps to keep the fastening system 870 from disengaging. The retaining element may include a raised portion, a lowered portion, a notch, a lip, a rough portion, etc. to prevent or at least inhibit the tab member 42 from undesirably slipping back through the slot member 44.

Frangible Bonding Agent

A frangible bonding agent is a bonding agent capable of forming a frangible bond suitable for use in the articles and/or fastening systems disclosed herein. In certain embodiments, the frangible bonding agent may comprise an adhesive such as, for example, a fugitive hot-melt adhesive. Suitable adhesives for use herein may include copolymers of 1-butene in an amount ranging from 10% to 80%; 20% to 70%; or even from 30% to 45% by weight based on the weight of the adhesive. Nonlimiting examples of suitable copolymers of 1-butene include copolymers of 1-butene and a member selected from the group consisting of ethylene, propylene and mixtures thereof. In certain embodiments, the concentration of 1-butene repeat units in the copolymer is in an amount ranging from 90% to 99%; 92% to 98%; or even 94% to 97% by weight based on the weight of the copolymer. In certain embodiments, the concentration of ethylene, and/or propylene repeat units in the copolymer may range from 1% to 10%; 3 to 9%; or even 4 to 8% by weight based on the weight of the copolymer. One particularly suitable example of a copolymer of 1-butene and ethylene may be purchased from Basell under the tradename PB-1. PB-1 is obtained by polymerization of 1-butene with a stereo-specific Ziegler-Natta catalyst to create a linear, high molecular, isotactic, semi-crystalline polymer.

Suitable adhesives for use herein may include a wax component. The term "wax" is recognized in the art and is intended to include any viscosity, speed of set, or rheology modifiers. Nonlimiting examples of wax include paraffin wax (e.g., high melt point and/or low melt point), microcrystalline wax, synthetic wax, such as fischer tropsch and polyethylene waxes and biproducts thereof (e.g., high melt point); or functionalized versions of these. Generally, low melt point waxes have melt points of no greater than 70° C., optionally 50-70° C. High melt point waxes have melt points of, for example, about 75 C-125° C. The adhesive may include both high melt point and low melt point waxes to provide a suitable crossover temperature (discussed in more detail below). In conventional fugitive adhesives, the ratio of high melt point to low melt point wax may be about 1:8, 1:10, 1:15 or even less. However, it is believed, without being limited by theory, that a greater amount of high melt point wax, relative to the amount of low melt point wax, may be important for providing a fugitive adhesive that can suitably withstand the manufacturing, packaging, transport and/or storage conditions typically associated with certain disposable absorbent articles. Ratios of high melt point wax to low melt point wax of from, for example, about 1:7 to 1:1; from 1:6 to 1:2; and from 1:5 to 1:3 by weight based on the total weight of the wax may be suitable for use herein. A ratio of high melt point wax to low melt point wax of 1:4 may be particularly suitable for achieving frangible adhesive bonds that do not exhibit an undesirable increase in bond strength when subjected to increased temperature and/or pressure conditions. The concentration of the wax in the adhesive may be in an amount of from 5% to 60% or from 10% to 40% by weight based on the weight of the adhesive. Various waxes suitable for use herein can be purchased from Exxon Mobil Chemical, Calumet, and Baker Petrolite. The wax, alone or in combination with other components may help reduce the viscosity of the composition, help make the composition easier to apply to the substrate, help provide faster speed of set for the composition, and/or lead to a subsequent crystallization of the adhesive as a result of its combination with the polymer in the adhesive composition (e.g., copolymer of 1-butene). It is believed, without being limited by theory, that the crystallization of a fugitive hot-melt adhesive results in a loss of cohesion with the passage of time, thereby allowing the adhesive to form a frangible bond. The initial bond strength of a bond formed by a fugitive adhesive is generally limited by the adhesive attraction between the adhesive and the substrate(s) to which it is applied (i.e., the intermolecular attraction between the adhesive and the substrate). However, after a fugitive adhesive crystallizes, the bond strength of the bond is generally limited by the cohesive strength of the adhesive, which is typically less, and in some instances substantially less, than the adhesive strength.

Suitable adhesives for use herein may include a tackifying resin component. The term "tackifying resin" is recognized in the art and is intended to include those substances that provide tack and specific adhesion to the adhesive. The tacky and adhesive properties provided by the resin may serve to secure elements to be bonded while the adhesive sets. The resin may also be used to reduce the viscosity of the adhesive, making the composition easier to apply to the substrate. The tackifying resin may be, but is not limited to, rosins, rosin derivatives, terpenes, modified terpene resins, hydrocarbons, or modified hydrocarbon resins, such as those known in the art. The concentration of the tackifying resin in the composition of the present invention may be in an amount ranging from 5% to 70%; 10% to 60%; 25% to 55% by weight based on the weight of the adhesive. Various tackifying resins can be purchased from Arizona Chemical, Exxon Mobil Chemical, and Eastman Chemical.

The adhesive may include optional ingredients such as antioxidants and/or colorants/pigments/dyes. An antioxidant may help stabilize the adhesive against degradation. The concentration of the antioxidant in the composition of the present invention may be in an amount ranging from 0.1% to 1% by weight of the adhesive.

Due to the wide range of environmental and processing conditions to which disposable absorbent articles may be exposed, a crossover temperature ($T_x$) of greater than 50° C.; for example, between 50°-70° C.; between 55°-65° C.; between 58°-62° C.; or even 60° C. may be suitable for certain adhesives described herein. $T_x$ is the temperature at which a hot-melt adhesive has the same apparent elastic modulus (G') and apparent viscous modulus (G"). The $T_x$ of an adhesive or other polymeric material may be determined according the Rheological Measurement Test detailed below. At temperatures below the $T_x$ of an adhesive, the adhesive may be more difficult or expensive to process (e.g., the adhesive does not flow as well or at all or additional energy must used), resulting in a smaller process window. Therefore, an adhesive that has a relatively low $T_x$, such as a conventional fugitive adhesive, may have desirable processing characteristics. However, at temperatures above the $T_x$, of such an adhesive, which may occur during transport and/or storage of an article comprising the adhesive, the adhesive may exhibit a greater tendency to flow and may penetrate further into the substrate to which it is applied, thereby causing an undesirable increase in bond strength. It is believed that the bonding agents disclosed herein may provide a solution to this problem.

Fugitive hot-melt adhesives are typically applied to a substrate at a temperature greater than the crossover temperature of the adhesive. Suitable fugitive hot-melt adhesives for use herein may exhibit a peak adhesive bond strength within one hour of application. Once the fugitive hot-melt adhesive cools, it typically begins to crystallize and may exhibit a decaying bond strength. As mentioned above, it is believed, without being limited by theory, that the decaying bond strength is due to the transition of the bond failure mode from adhesive failure to cohesive failure (i.e., the fugitive adhesive forms a frangible bond). Suitable bond strength decays for a fugitive adhesive include a loss of greater than or equal to about any of the following amounts of initial bond strength: 20%, 30%, 40%, 50%, 55%, 60%, 65%, 70%, 75%, 80%, 85%, 90%, 95%, or 100%. The bond strength decay of a fugitive adhesive may be determined according to the Coupon Peel Test described below.

Improved Fastening System

Disposable absorbent articles such as those described herein are often manufactured on a high speed production line capable of producing more than 400 products per minute. High speed manufacturing lines are typically designed to be as compact as possible to minimize the amount of space required for the process equipment. Thus, a typical manufacturing process may subject an article such as a disposable diaper to a tortuous process path at a relatively high rate of speed. During the high speed production of disposable absorbent articles, portions of the article that extend out too far in the CD may be damaged and/or contaminated by the process equipment. Similarly, unsecured portions of the article that do not extend out in the CD may still exhibit undesirable changes in position (e.g., "flapping" or "bouncing" around) in response to the speed and/or direction of the line. In order to reduce the risk of such undesirable occurrences, portions of the article (e.g., ears, fastening tabs, tab members, slot members, engaging members, and the like) may be folded over and/or fastened to themselves and/or another absorbent article portion at some point during the manufacturing process. It may be desirable that the folded portions remain folded during the production run. By including a suitable bonding agent in the fastening system, the bond strength of a folded fastening system may be temporarily increased such that the fastening system is maintained in a folded configuration for a predetermined amount of time (e.g., throughout a portion or even all of the production process of an article).

In certain embodiments, a frangible bonding agent may be disposed on one or more portions of the ear (e.g., the fastening tab, engaging member and/or engaging elements). The ear and/or fastening tab may then be manipulated (e.g., folded) such that the frangible bonding agent, by itself or in combination with another fastening mechanism, joins one portion of the ear and/or fastening tab to another portion. For example, the frangible bonding agent may be applied to at least some of the heads of mushroom-shaped engaging elements disposed on the engaging member of a fastening tab. In this example, the fastening tab may be folded over such that the frangible bonding agent contacts another portion of the same surface of the fastening tab that the engaging member is disposed on. In another example, a frangible bonding agent may be applied to the tab member of a slot/tab type mechanical fastening system, and then the tab member may be joined to itself, the slot member, and/or other portions of the fastening system. When applying the frangible bonding agent to a fastening system, it may be desirable to apply the frangible bonding agent such that it does not interfere with the ability of the fastening system to be fastened and/or refastened as intended. For example, applying the frangible bonding agent to a relatively large number of the hooks may interfere with the ability of the hooks to engage with a receiving member. Thus, it may be desirable to apply the frangible bonding agent to 10% or less of the hooks (e.g., 9%, 8%, 7%, 6%, 5%, 4%, 3%, 2%, or even less than 1%), as measured by the % surface area of the hook-containing portion of the engaging member that includes the frangible bonding agent. The frangible bonding agent may be present as an unbroken strand or film that extends between two more engaging elements. The frangible bonding agent may be present in any suitable linear or nonlinear pattern such as, for example, a pattern that resembles one or more straight lines, one or more broken lines, S-shapes, T-shapes, X-shapes, omega-shapes, dots, circles, rectangles, spirals, combinations of these and the like. In one suitable example, the frangible bonding agent may be applied as substantially straight line (i.e., bead) of fugitive hot-melt adhesive that has a length of between 1% and 100%; 1 and 50%; 1 and 40%; or even 1 and 20% of the length of the engaging member. In order to potentially minimize the effect of the frangible bonding agent on the ability of the fastener to be fastened or refastened, the frangible bonding agent may be applied as a relatively narrow line having a width of between 0.1% and 30%; 1 and 25%; 1 and 15%; or even 1 and 10% of the width of the engaging member. Of course, the frangible bonding agent may have any suitable length or width desired, as long as suitable bond strengths and fastener performance is obtained. In certain embodiments, the frangible bonding agent may be contiguous with one or more of the edges of the engaging member and/or fastening system. For example, the frangible bonding agent may extend from one edge of the engaging member to another edge in the MD, CD, and/or diagonally, or the frangible bonding agent may extend from one edge of the engaging member and/or fastening system to an inner portion of the engaging member and/or fastening system (i.e., a portion disposed between two edges), but not to another edge. In certain embodiments, the frangible bonding agent may be contained entirely within the boundaries that define the x-y plane of the engaging member and/or the fastening system. In certain embodiments, the frangible bonding agent may be disposed adjacent the engaging member rather than on the engaging member so as to reduce or even eliminate any undesirable impact that the frangible bonding agent may have on the intended mechanical bonding function of the fastening system, such as fouling of the engaging elements. In certain embodiments, the frangible bonding agent may be disposed on a surface of the fastening system to which the engaging member is to be joined. For example, the frangible bonding agent may be applied to a nonwoven surface of an ear and/or fastening tab, such that when the fastening tab is folded the engaging member comes into contact with the frangible bonding agent. In certain embodiments, the frangible bonding agent may be disposed on both the engaging member and one or more other portions of the fastening system. For example, the frangible bonding agent may be applied as a single line of adhesive disposed on both the engaging member and a portion of the ear and/or fastening tab adjacent the engaging member. In another example, the frangible bonding agent may comprise a first line of adhesive disposed on the engaging member and a second line of adhesive disposed on another portion of the fastening system spaced apart from the first line and the engaging member. Examples of suitable patterns and configurations for applying the frangible bonding agent are described in U.S. Pat. No. 6,701,580, issued to Bandyopadhyay on Mar. 9, 2004.

In certain embodiments, a bonding agent that does not form a frangible bond, but exhibits a suitable decaying bonding strength may be used herein. In such embodiments, the bonding agent may fail adhesively or cohesively as long as suitable bonding forces and fastener performance are provided.

The bond strength of an engaged fastening system may be characterized herein as an opening force (Initial or Aged), when measured according to the Opening Force Test, or as a Modified Opening Force (Initial or Aged), when measured according to the Modified Opening Force Test, both of which tests are described in more detail below. It is to be understood that both characterizations refer to the amount of force required to disengage or open an engaged fastener or break a frangible bond. Suitable bonding agents for use herein may exhibit decaying bond strength. Thus, the bonding agent may provide a suitable preliminary bond strength for a folded fastener, pre-engaged fastener, or other pre-positioned article component during the production process, since this bond strength is needed for only several minutes or less (e.g., less than 5 minutes or even less than a few seconds). However, it may desirable to have a relatively high preliminary bond strength for up to an hour in the event of, for example, unplanned line stoppages or other unexpected events. It is believed that the Initial Modified Opening Force and Initial Opening Force described below represent this preliminary bond strength. In certain embodiments, a suitable Initial Modified Opening Force and/or Initial Opening Force for the fastening systems and/or frangible bonds described herein may be greater than 2 N; 3 N; 4 N; 5N; 6 N; 7 N; 8 N or even greater than 10 N. To provide a suitable absorbent article to a consumer, however, it may be desirable for the preliminary bond strength to decay to a second lower bond strength by the time the article is used by the consumer (e.g., more than 1 day, 5 days, or even 1 month after production of the article). It is believed that the Aged Modified Opening Force and Aged Opening Force represent this second lower bond strength. In certain embodiments, a suitable Aged Modified Opening Force and/or Aged Opening Force for the fastening systems and/or frangible bonds described herein may be less than 8N; 5N; 2 N; 1.5 N; 1 N; 500 mN; or even less than 100 mN. When a consumer attempts to use an article that includes an improved fastening system as described herein, it may be desirable that there is only a slight or even no noticeable increase in the amount of force required to open the improved fastening system, as compared to a conventional fastening system. Thus, it may be desirable that the force required to open an aged fastening system, which has been treated with a frangible bonding agent as described herein ("treated fastening system"), is no more than 40%, 30%, 20%, 15%, or even 10% greater than the force required to open an untreated fastening system. In certain embodiments, the force required to open a treated fastening system may be the same as or even less than the force required to open an untreated fastening system.

It is commonly known that at least some fasteners such as hook/loop type mechanical fasteners have a peel force component and a shear force component when fastened. The peel force component is generally associated with a force that is exerted perpendicular to the plane of the fastener such as, for example, the force exerted by a user when attempting to unfasten or unfold the fastener. The peel force component of a fastened fastening system may be measured by, for example, the Opening Force Test. The shear force component of a fastened fastening system, on the other hand, is generally associated with a force that is exerted parallel to the plane of the fastener such as, for example, the force(s) typically exerted on the fastener when the diaper is worn as intended. The shear component may be measured by the Shear Test described in more detail below. It may be undesirable for a bonding agent to interfere with the intended function of the fastening system of an article by reducing the amount of shear force that a fastened fastener can withstand before becoming unfastened. Therefore, when including a bonding agent in a mechanical fastening system, it may be desirable to apply the bonding agent such that the Shear value of a treated fastening system is at least 50%; 60%; 70%; 80%; or even 90% of the Shear value of an untreated system, when measured according to Shear Test. In certain embodiments, the Shear value of a treated fastening system may be the same as or even greater than the Shear value of an untreated system, when measured according to Shear Test.

Figure 5:
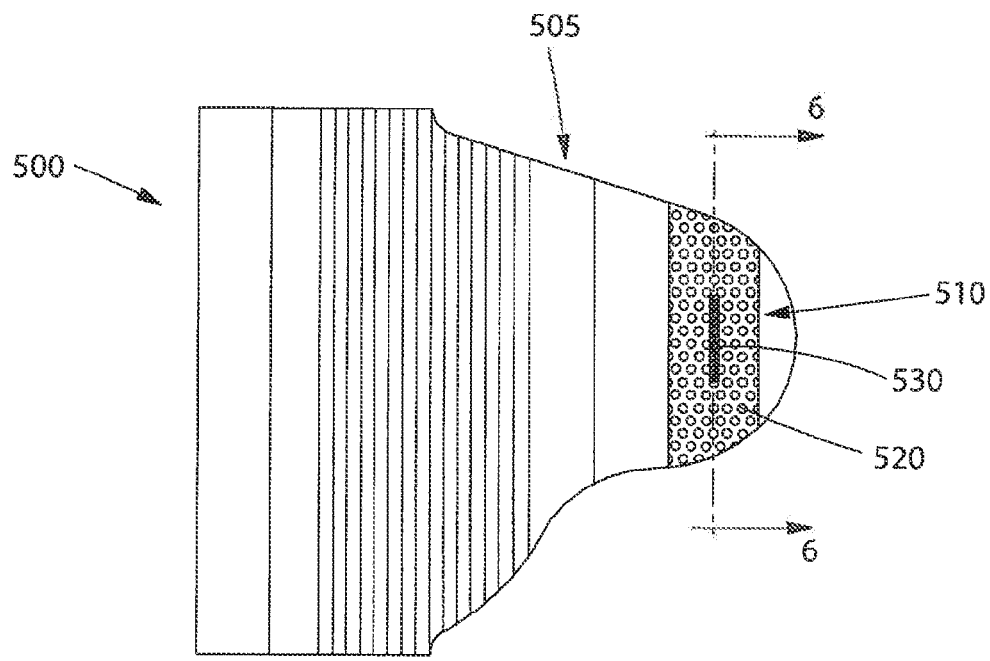
FIG. 5 is a plan view of an ear and a fastening tab.

FIG. 5 shows a plan view of an ear 500 for a hook/loop type mechanical fastening system. The ear 500 may include fastening tab 505, an engaging member 510 and a plurality of engaging elements 520 extending out of a base 675. The fastening tab may include a bonding agent 530 disposed on at least some of the engaging elements 520. As shown in FIG. 5, the bonding agent 530 may be applied in the form of a substantially straight, unbroken line bounded by the engaging elements 520.

Figure 6:
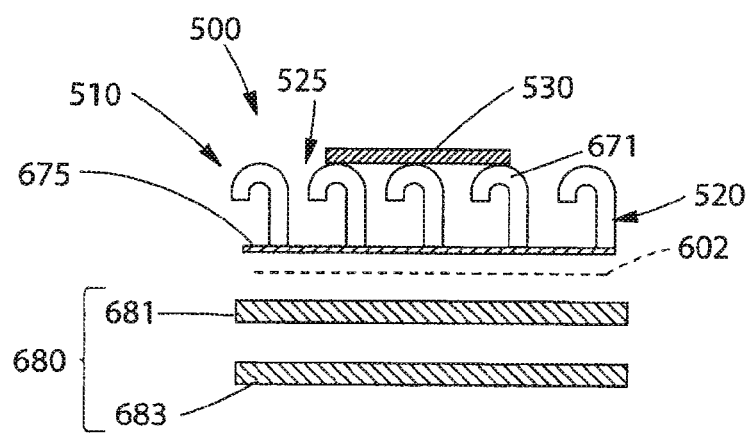
FIG. 6 is a schematic cross-section view of the fastening tab of FIG. 5 along line 6-6.

FIG. 6 shows a schematic cross-section view of the ear 500 of FIG. 5 along line 6-6. The engaging elements 520 of FIG. 6 are shown as being hook-shaped, however, it is to be understood the engaging elements 520 may be any suitable shape, as desired. The ear 500 may include a support member 680 formed as a laminate comprising an upper and a lower nonwoven layer 681 and 683. The fastening tab 505 may include the support member 680 and/or one or more additional nonwoven and/or film components. The base 675 of the engaging member 510 may be joined to the upper nonwoven layer 681, for example, by adhesive layer 602. The bonding agent 530 may be applied to the heads 671 of the engaging elements 520 as a substantially unbroken line that spans the gaps 525 between adjacent engaging elements 520. When the bonding agent 530 is applied as a molten composition, the bonding agent 530 may at least partially penetrate into one or more of the gaps 525, but remain substantially continuous (i.e., unbroken).

Figure 7A:
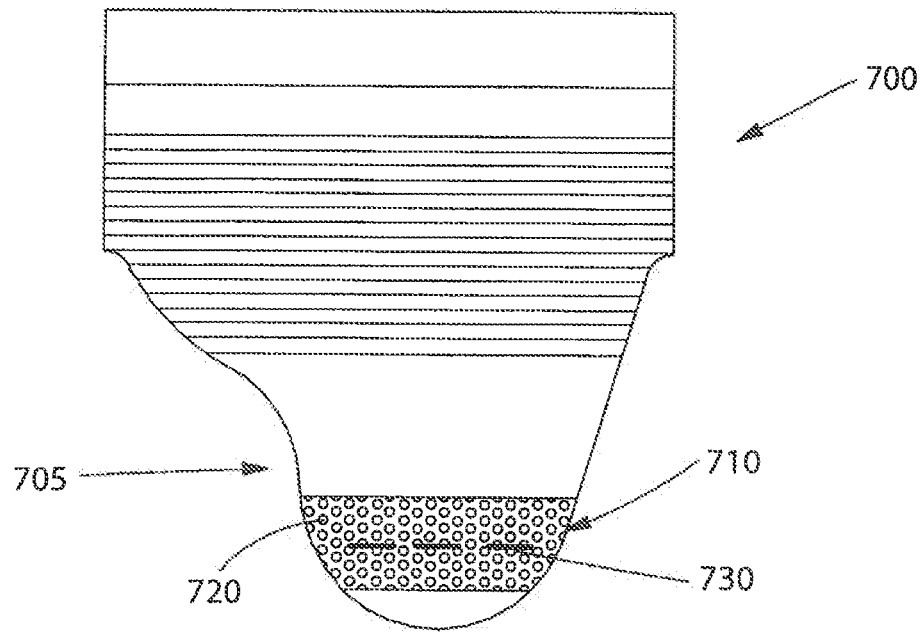
FIGS. 7A-7D are plan views of examples of a fastening tab.
Figure 7B:
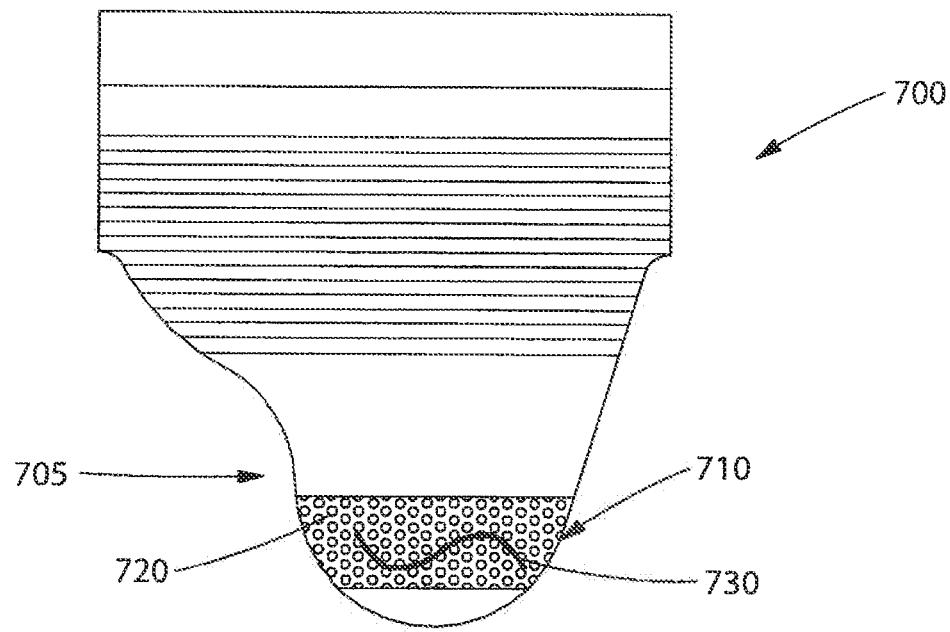
Figure 7C:
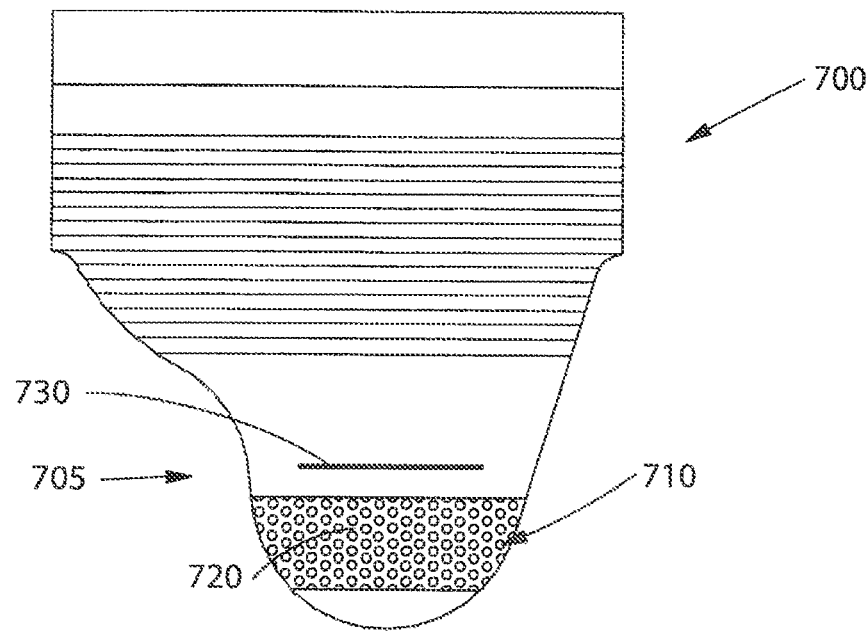
Figure 7D:
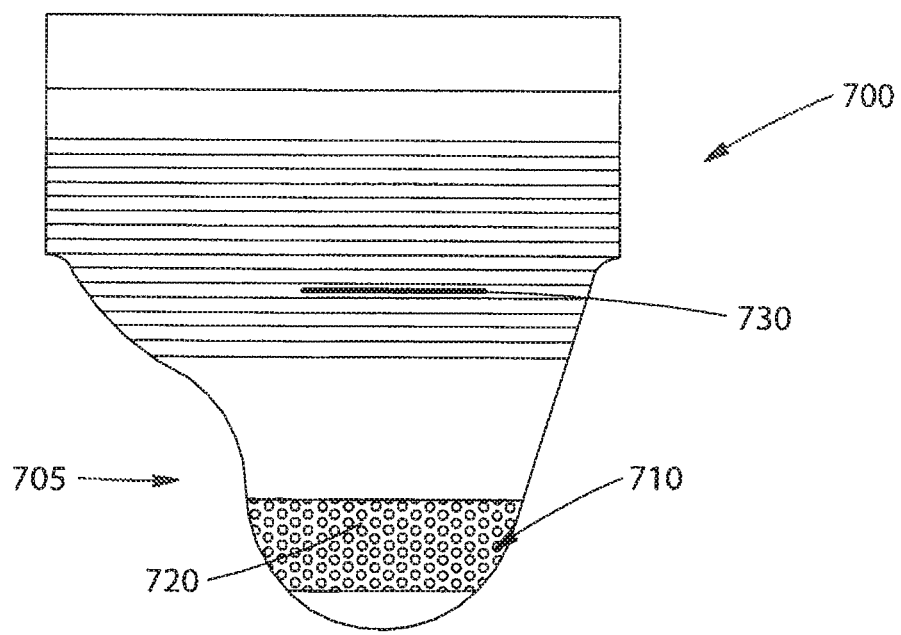

FIGS. 7A-7D show examples of bonding agent 730 patterns on an ear 700. The ear 700 may include a fastening tab 705 comprising an engaging member 710 and engaging elements 720. The ear 700 may also include a bonding agent 730. FIG. 7A shows the bonding agent 730 disposed on the engaging elements 720 in the pattern of a broken line. FIG. 7B shows the bonding agent 730 disposed on the engaging elements 720 in an "S-shape." FIG. 7C shows the bonding agent 730 disposed on a first portion of the ear 700 adjacent to the engaging member 710 in the pattern of a continuous line. The ear 700 in FIG. 7C may be manipulated (e.g., folded) in order to contact the bonding agent 730 with a second portion of the ear 700. FIG. 7D shows the bonding agent 730 disposed on a first portion of the ear 700, which is spatially separated from the engaging member 710 (i.e., not adjacent to the engaging member 710). The bonding agent 730 in FIG. 7D may be positioned such that when the fastening tab 705 is manipulated (e.g., folded) the fastening tab and/or engaging member 710 contacts the bonding agent 730.

Figure 7E:
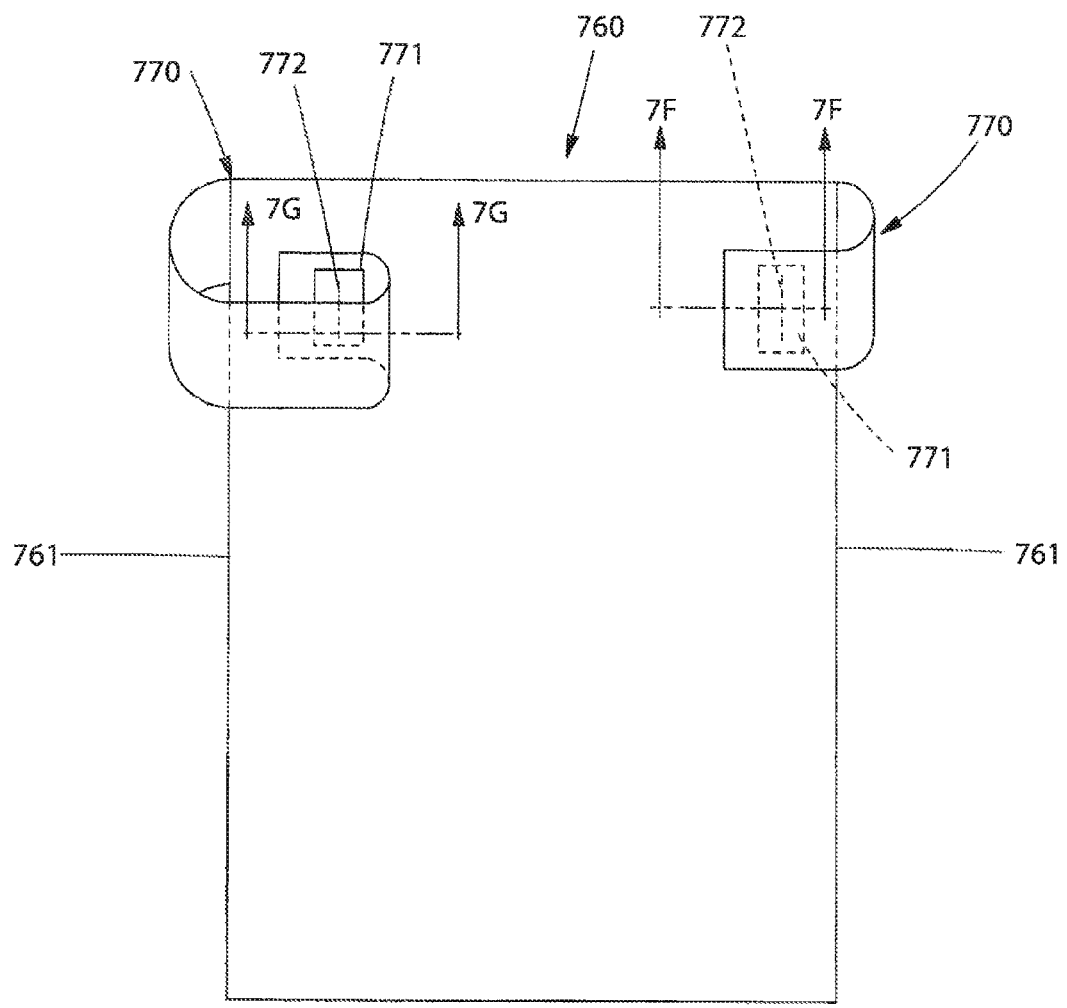
FIG. 7E is plan view of a disposable absorbent article.
Figure 7F:
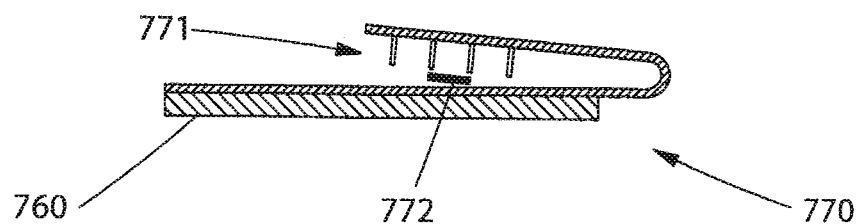
FIG. 7F is a schematic cross-section view of the fastening tab of FIG. 7E along line 7F-7F.
Figure 7G:
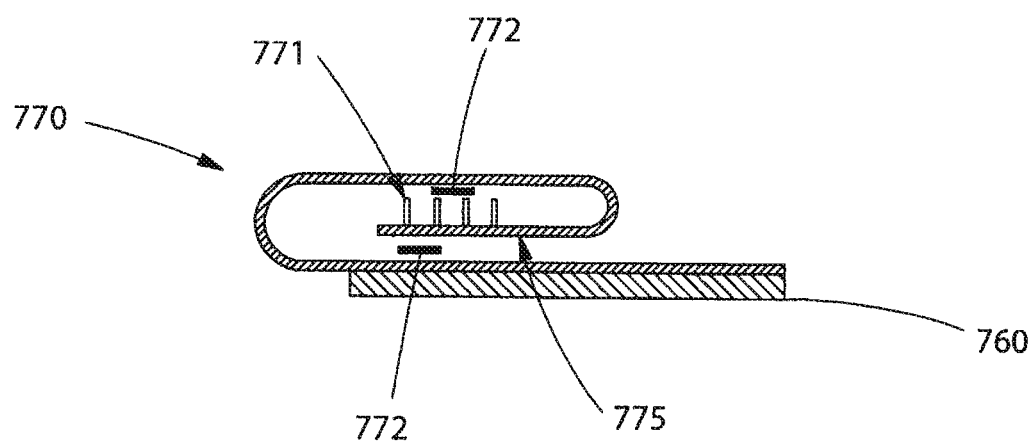
FIG. 7G is a schematic cross-section view of the fastening tab of FIG. 7E along line 7G-7G.

FIGS. 7E, 7F, and 7G show examples of folded fastening tab 770 configurations. FIG. 7E shows an absorbent article 760 in a flat-out configuration. The absorbent article 760 includes a pair of fastening tabs 770 disposed along opposing longitudinal side edges 761 of the article 760, wherein each fastening tab 770 is folded in a different configuration. The fastening tabs 770 each include an engaging member 771 and a bonding agent 772. In the example shown in FIG. 7F, the bonding agent 772 is disposed on the engaging member 771. The fastening tab 770 may be folded laterally inwardly, as shown in FIG. 7F, such that the bonding agent 760 contacts a portion of the absorbent article 760 or another portion of the fastening tab 770. In the example shown in FIG. 7G, the bonding agent 772 is disposed on the engaging member 771 and on the non-engaging member side 775 of the fastening tab 770 (i.e., the side of the fastening tab 770 opposed to the side on which the engaging member 771 is disposed). The fastening tab 770 may be folded twice laterally inwardly, as shown in FIG. 7G, such that the bonding agent disposed on the engaging member 770 contacts a first portion of the fastening tab 770 or article 760 inboard of the engaging member and the bonding agent 773 disposed on the non-engaging member side 775 of the fastening tab 770 contacts a second portion of the fastening tab 770 or article 760 inboard of the first portion. It is to be understood that, with regard to FIGS. 7E-7G, the term inboard refers to the relative positions of elements when the article 760 and the fastening tabs 770 are viewed in a flat-out configuration (i.e., not folded).

In certain embodiments, it may be desirable to temporarily join portions of a slot/tab type mechanical fastening system to one another or to another portion of the article (e.g., to keep these elements from undesirably moving around during manufacturing and/or to position the elements consistently and/or conveniently for a consumer to use). For example, it may be desirable to join the tab to an inwardly facing portion of the absorbent article chassis in the vicinity of the slot so that a consumer may become accustomed to finding the tab positioned in substantially the same location each time the consumer uses to the article. In this example, the tab may be joined to the chassis portion with a frangible bonding agent so that the consumer may easily detach the tab from the chassis and insert it into the slot for use. In addition, the bonding agent desirably provides sufficient bonding strength to maintain the article in a desired configuration for a predetermined amount of time (e.g., during manufacturing and/or packaging). It is to be understood that embodiments wherein the slot and/or tab are joined to each other, themselves, or any other portion of the article are also contemplated herein.

Figure 10:
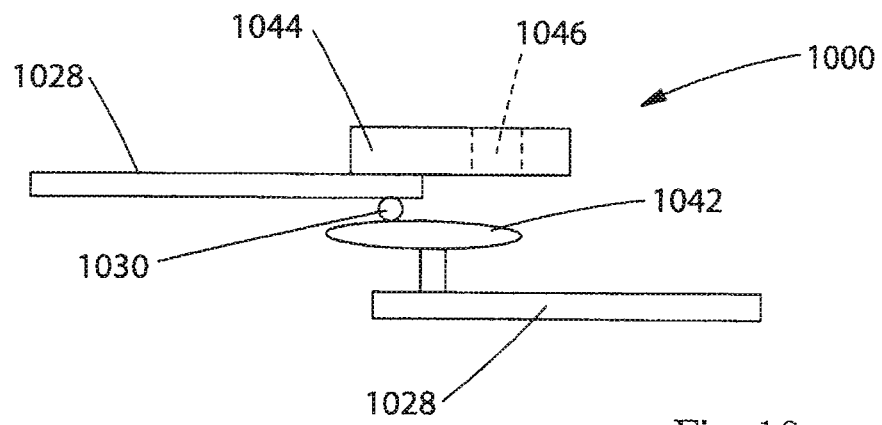
FIG. 10 is a schematic view of a fastening system.

FIG. 10 shows a side view of a slot/tab type mechanical fastening system 1000. The fastening system 1000 may include a slot member 1044 and a tab member 1042, each joined to a support member 1028 (e.g., nonwoven and/or film). The slot member includes a slot 1046 configured to pass the tab member 1042 therethrough. The support member 1028 may be joined to or be part of another article component (e.g., a side panel of a disposable diaper). In certain embodiments, the fastening system may include a bonding agent 1030 disposed on a component of the fastening system (e.g., the tab member 1042, the slot member 1044, and/or the support member 1028). For example, the bonding agent 1030 may be disposed on the tab member 1042 such that the tab member 1042 may be joined to itself or another component of the fastening system 1000 (e.g., slot member 1044 and/or support member 1028).

While particular examples are disclosed that describe portions of a fastening system joined to themselves, one another, or even other portions of an absorbent article, it is to be understood that embodiments wherein absorbent article components other than fastening system components are positionally maintained by a bonding agent are contemplated herein. For example, disposable absorbent articles such as diapers, pants, and pant-like articles typically include an element for inhibiting or preventing the leakage of bodily exudates such as urine from the leg opening of the article. Such elements are sometimes referred to as barrier leg cuffs ("BLCs") or cuffs. BLCs may be disposed on the wearer facing side of an absorbent article, inboard of the longitudinal side edges. The BLCs are generally intended to provide a barrier to restrain the free flow of body exudates before the flowing exudates reach the longitudinal sides and provide a structure to hold and contain such exudates within the absorbent article. BLCs may be functionally distinguished from so-called gasketing cuffs. Gasketing cuffs typically remain in the plane of the absorbent article and form a seal against leakage by drawing the diaper against the wearer's skin. BLCs, however, are typically intended to be disposed out of the plane of the absorbent article (i.e., the plane in which body exudates will flow) and thereby provide a barrier or dam against leakage. Thus, liquid such as urine flowing across the topsheet will encounter the BLC and be stopped. Nonlimiting examples of suitable BLC materials and configurations are disclosed in U.S. Pat. Nos. 4,738,677 to Foreman; and 5,021,051 to Hiuke.

Each barrier leg cuff may be formed from a flexible material and joined to, for example, the topsheet or chassis of the absorbent article on the wearer facing side of the article. The BLC may have a proximal edge, an opposing distal edge, and a body connecting the proximal and distal edges. The BLC may include a spacing means that, when activated, causes the distal edge of the BLC to extend away from the proximal edge of the BLC and out of the plane of the diaper. In certain embodiments, the spacing means may comprise one or more contractible, elastic strands that extend along the distal edge of the BLC and are anchored to the longitudinal ends of the absorbent article. For example, the distal edge of the BLC may be folded around the elastic strand(s), thereby forming a tunnel through which the elastic strand extends. Thus, when the elastic strand(s) are stretched, the distal edge of the BLC is lifted out of the plane of the diaper by the tensioned elastic strand. Generally, the higher the dam formed by the BLC, the more effective it is. Therefore, the greater the width (i.e. the distance between the proximal and distal edges) of the barrier leg cuff, the more effective the barrier leg cuff will be. However, when a relatively high BLC is used in conjunction with a prefastened absorbent article such as a pant, the BLC may undesirably interfere with the donning of the absorbent article. For example, when putting a pant on a wearer, a caregiver may need to enlarge the waist opening to provide sufficient space for inserting a wearer's feet and/or legs. The force applied by the caregiver to enlarge the waist opening may cause the BLC to extend at least partially out of the plane of the pant. Thus, when the caregiver or wearer then attempts to position the feet of the wearer into the leg holes of the pant, a portion of the wearer's foot (e.g., toes or heel) may get caught or entangled by the BLC, thereby causing undesirable damage to the BLC and/or inconvenience to the caregiver and/or wearer. Therefore, it may be desirable to keep the distal edge of the BLC from extending out of the plane of the absorbent article while attempting to put it on a wearer.

Bonding one or more portions of the BLC to another portion of the article such as a portion of the topsheet and/or chassis may prevent the distal edge of the BLC from extending out of the plane of the article while the article is being donned. However, unless this bond is broken, the BLC may not provide the desired barrier function during the normal use of the article. Using a frangible bonding agent to provide the bond may maintain the BLC in an inactivated configuration (i.e., a configuration where the distal edge is unable to extend out of the plane of the diaper) while the article is being donned, and the relatively weak bond provided by the frangible bonding agent may be broken by a user to activate the BLC. In certain embodiments, the bond may be configured to have different bond strengths, depending on the direction in which the frangible bonding agent is applied to the BLC. That is, the bond may exhibit higher bond strengths depending on the direction of an applied force such that the bond is stronger in certain directions than other directions. For example, it is believed, without being limited by theory, that a frangible bonding agent such as a fugitive adhesive may be applied to the BLC in the lateral direction in order to maximize the bond strength in the lateral direction. Thus, when a force is applied to the article in the lateral direction (e.g., when a caregiver attempts to expand the waist opening for inserting a wearer's foot therein), the BLC may remain bonded to the article and not be activated. However, it is believed that the bond strength of the bond will be the weakest in the longitudinal direction, and therefore by applying a suitable amount of force in longitudinal direction (e.g., by pulling the front and rear waist panels away from one another), the bond may be broken and the BLC activated. In certain embodiments, the bond may exhibit sufficient strength to keep the BLC inactivated during donning of the article but may be broken, for example, when the caregiver inserts a finger through the leg opening and manipulates the BLC (e.g., slides the finger along the BLC) such that the bond is broken.

Figure 11:
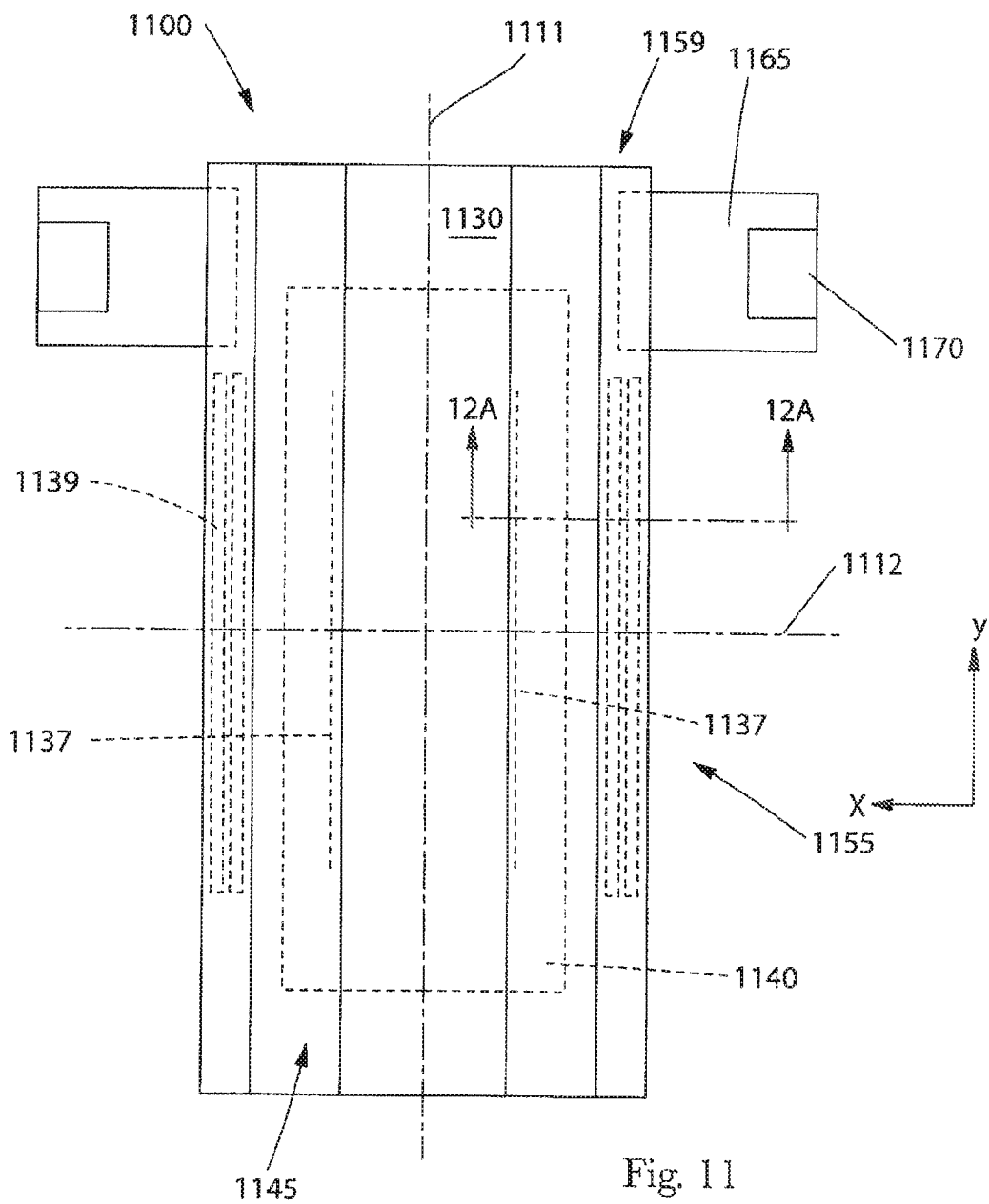
FIG. 11 is a plan view of a disposable absorbent article.

FIG. 11 shows an absorbent article 1100 in a flat-out configuration (i.e., no elastic induced contraction) with the garment facing side 1145 facing the viewer and the opposing wearer facing side 1146 facing away from the viewer. The absorbent article 1100 has a longitudinal centerline 1111 that extends in the longitudinal direction y of the absorbent article 1100, and a lateral centerline 1112 that extends in the lateral direction x of the absorbent article 1100 and is orthogonal to the longitudinal centerline 1111. The absorbent article 1100 may include a topsheet 1120, a backsheet 1130, and an absorbent member 1140 disposed between the topsheet 1120 and backsheet 1130. The absorbent article 1100 may include one or more ears 1165, which each may include one or more fastening system elements such as fastening tab 1170. The fastening tab 1170 in FIG. 11 is shown in a folded configuration, but it is to be understood that fastening tab 1170 may be configured to extend laterally outwardly from the ear 1165. In certain embodiments, the fastening tab 1170 may instead be an engaging member, as described herein, joined to the ear 1165. In certain embodiments, the ear 1165 may be folded or otherwise manipulated to reduce the distance that it extends laterally outwardly from the absorbent article 1100. The absorbent article may include a gasketing cuff 1160 disposed along one or both longitudinal side edges 1155. The gasketing cuff 1160 may include one or more elastic strands 1139 or other known tensioning means (e.g., elastic films, nonwovens, or adhesives) for providing the requisite tensioning force to form a seal between the outer surface of the gasketing cuff 1160 and the body of a wearer. The absorbent article 1100 may include a BLC 1150. The BLC 1150 is generally disposed inboard of the gasketing cuff 1160 (i.e., closer to the longitudinal centerline 1111 than the gasketing cuff 1160 in the lateral direction x). The BLC 1150 may include one or more elastic strands 1137 or other tensioning means for providing the requisite tension to lift the BLC 1150 out of the plane of the absorbent article 1100. The elastic strands 1137 of the BLC 1150 may be anchored (i.e., joined) to the absorbent article in any suitable configuration known in the art (e.g., proximate to one or both end edges 1159).

Figure 12A:
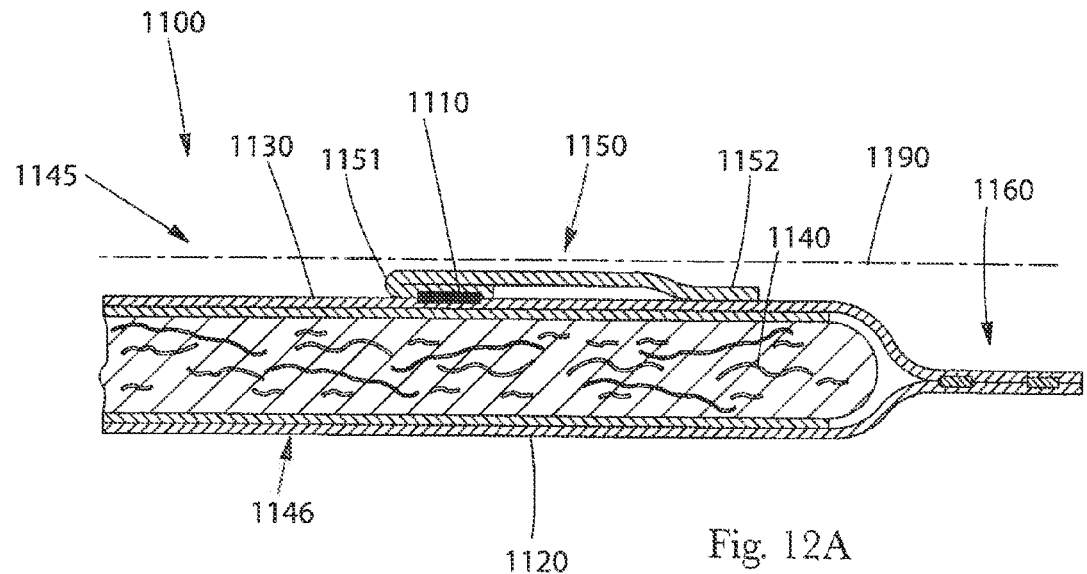
FIGS. 12A-12B are schematic cross-section views of the disposable absorbent article of FIG. 11 along line 12A-12A.
Figure 12B:
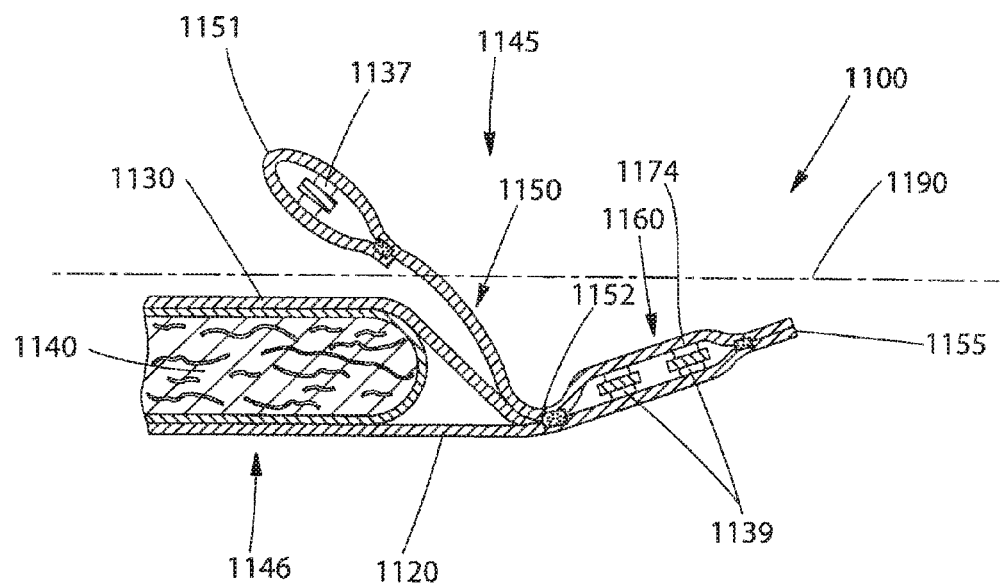

FIG. 12A shows a schematic cross-section of an exemplary configuration of the absorbent article 1100 of FIG. 11 along line 12A-12A. As shown in FIG. 12A, the distal and proximal ends 1151 and 1152, respectively, of the BLC 1150 may both be joined to a portion of the absorbent article 1100. In this example, the proximal and distal ends 1152 and 1151 are both joined to the topsheet 1120. The distal end 1151 of the BLC 1150 may be joined to the topsheet 1120 with a frangible bonding agent 1110. It may be desirable to join the proximal end 1152 of the BLC 1150 to the topsheet or other absorbent article portion with a permanent bonding agent, such as is commonly known in the art. One or more portions of the BLC 1150 may be joined to any suitable portion of the absorbent article 1100 desired, such as the backsheet 1130. In certain embodiments, the proximal end 1152 may include a flap 1174 that extends past the edge of the absorbent member 1140 to form a portion of the gasket cuff 1160 (as shown in FIG. 12B). The flap 1174 may be joined to the backsheet 1130 along the longitudinal side edge 1155 of the absorbent article 1100. When in a temporarily bonded configuration, as shown in FIG. 12A, the BLC 1150 may be substantially parallel to the plane of the absorbent article 1100, which is represented by line 1190. While this example may depict the distal end of the BLC being joined to the topsheet with a frangible bonding agent, it is to be understood that embodiments wherein a bonding agent spans the entire distance between the distal and proximal ends of the BLC or any portion thereof are also contemplated herein.

FIG. 12B shows a schematic cross-section of an exemplary configuration of the absorbent article 1100 of FIG. 11 along line 12A-12A. As shown in FIG. 12B, the BLC 1150 and the topsheet 1120 are no longer bonded to one another by the frangible bonding agent 1110, as described and shown above in FIG. 12A. The temporary bond may be broken by one or more of the methods described herein or any other suitable means known in the art. Once the bond is broken, the distal end 1151 of the BLC 1150 may now extend out of the plane 1190 of the absorbent article 1100 (i.e., the distal end 1151 is positioned such that the BLC 1150 is no longer substantially parallel to the plane 1190), and the BLC 1150 may perform its intended barrier function.

Table 1 below illustrates the effect that applying a frangible bonding agent has on the Shear value of a hook/loop type mechanical fastening system. Table 1 shows Shear values for two different bonding agent amounts per ear and for unprocessed hook material. The Shear values provided in Table 1 refer to a peak load, reported in Newtons, as determined by the Shear Test. All of the values shown are calculated as an average of 10 ears. The treated samples are obtained as follows (refer to FIG. 13). Aplix 963 brand hook material 1371 is joined to a diaper ear 1370 via a permanent bonding adhesive in a typical high speed diaper manufacturing process. In the same process, the hook material 1371 is then treated with a 12 mm long line of a frangible bonding agent 1330, which in this case is PHO-3005 type fugitive hot-melt adhesive available from H.B. Fuller. The bonding agent 1330 is applied in a pattern substantially similar to the one shown in FIG. 13. An eDot brand hot-melt adhesive applicator available from Nordson Corporation is used to apply the frangible bonding agent 1330 at a temperature of 179° C. The applicator has a nozzle opening of 0.25 mm. The ear 1370 is folded over such that the frangible bonding agent 1330 contacts another portion of the ear 1370. By way of example, the ear 1370 in FIG. 13 may be folded in the x-direction about line 1386 to obtain such a configuration. The folded ear is fed through a pair of rotating rolls that form a nip set to exert a pressure of 207 kilopascals to the sample. Ten ears should be made for testing and allowed to cool. After 7 days at 22°+/−3° C., the folded ear is unfolded such that the adhesive bond formed between the hook material and ear is broken. The samples are then prepared for the Shear Test as described in that test method. The receiving member in the test is a 25 gsm knit material, available from Nordenia International AG, Germany.

TABLE 1

| Sample Description | Bonding Agent Weight per Ear [mg/ear] | Shear Test Peak Load [Newtons] |
|---|---|---|
| Diaper Ear with Bonding Agent | 0.6 | 25.1 |
| Diaper Ear with increased level of Bonding Agent | 1.1 | 26.1 |
| Hook Raw Material | 0 | 25.7 |

Table 2 below illustrates the crossover temperatures of several bonding agents. The first bonding agent is a fugitive hot-melt adhesive sold under the product code PHO-3005. The second bonding agent is a fugitive hot-melt adhesive sold under the product code PHO-3000. The third bonding agent is a permanent hot-melt adhesive sold under the product code D-3166. All three adhesives are available from H.B. Fuller.

The crossover temperature of each bonding agent is determined according to the Rheological Measurement Test, except that the plate gap target is 1,789 μm for PHO-3000 and 1,743 μm for PHO-3005.

TABLE 2

| Bonding Agent | Crossover Temp ($T_x$) |
|---|---|
| PHO 3005 | 58-62° C. |
| PHO 3000 | 45-50° C. |
| D3166 | 73-77° C. |

Figure 13:
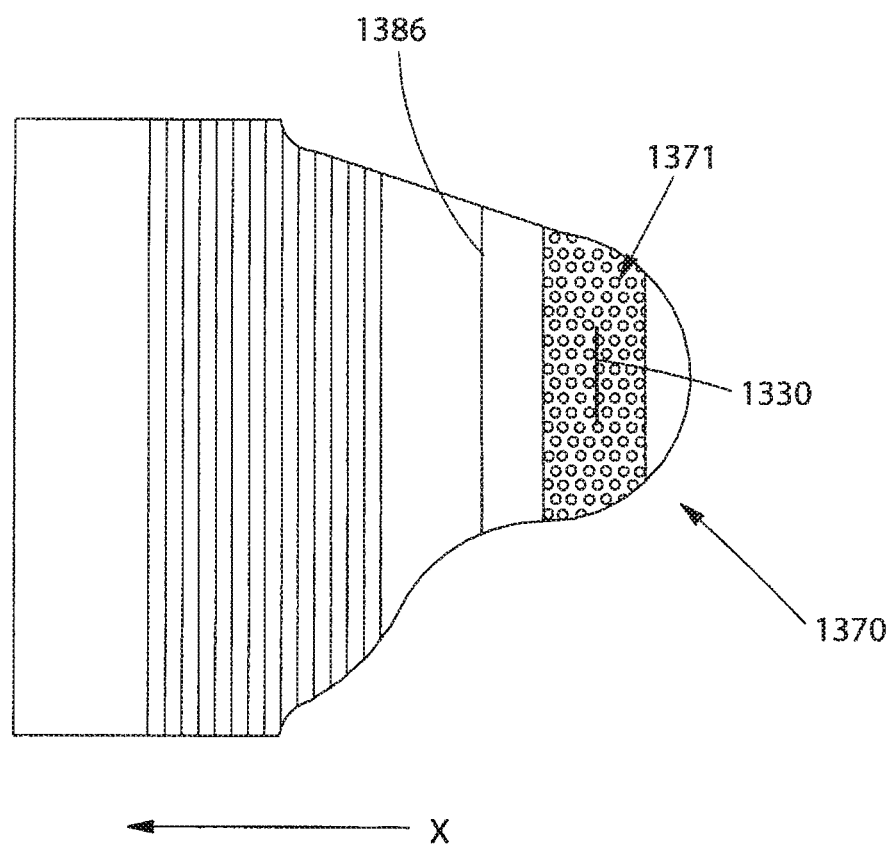
FIG. 13 is a plan view of an ear and a fastening tab.

Table 3 below illustrates the effect that temperature and/or pressure may have on the bond strength of an adhesive. PHO-3000 and PHO-3005 are both fugitive adhesives, while H2401 is a permanently bonding adhesive available from H.B. Fuller. The adhesives are applied to a substrate (e.g., nonwoven, film, or hook material) as described below. The adhesive types, amounts, and type of material for preparing each sample is indicated in the Table. The hook types shown in Table 3 are either Applix 963 brand hooks ("963"), hooks sold under the product code CHK00732 by 3M ("732"), or hooks sold under the product code CHK01088 by 3M ("88-1"). Samples 1-3 and 5-8 are prepared by applying the respective adhesive shown in Table 3 to the respective hook material shown in Table 3. The adhesive is applied as a continuous line in the center of the hooks to obtain the amount indicated in Table 3. Samples 1-3 include PHO-3005; samples 5-6 include a PHO-3000; and samples 7-8 include H2401, as these adhesives are described above. Sample 4 is an ear 1370 as illustrated in FIG. 13, except that sample 4 does not include an engaging member 1371 (i.e., hook material). The ear of sample 4 is an activated (i.e., incrementally stretched), four-layer laminate of a 65 micron film sandwiched between a layer of 27 gsm carded nonwoven and a layer of 17 gsm SMS nonwoven, and a 40 gsm spunbond nonwoven layer joined to the 27 gsm nonwoven layer. The PHO-3000 is applied to the 27 gsm nonwoven portion of laminate in two parallel stripes. The stripes are positioned in substantially the same way as the edges 1391 and 1392 of the engaging member 1371 are positioned in FIG. 13. The ear 1370 is then folded along folding line 1386 and stamped with a clicker press (e.g., model SE 25L available from Atom S.p.A., Italy or equivalent) configured to apply a pressure of 46.1 kPa to the entire folded ear. Samples 1-3 and 5-8 are conditioned as follows. A size 4 PAMPERS CRUISERS brand disposable diaper is placed in a LEXAN brand polycarbonate box having a storage space that is 45 mm deep, 165 mm long and 125 mm wide. Up to 3 sample substrates (i.e., ears) are placed on the outside of a pad of a bifolded diaper, and another bifolded diaper placed over the sample. Up to another 3 substrates are placed on the second diaper pad, and a third diaper is placed on top of this second group of samples. This process is repeated until a total of 5 diapers are stacked in the box. Since the stack of 5 diapers extends out of the box, a lid is placed over the diapers and a C-clamp used to hold the lid shut. The C-clamp is configured to apply 830 Pascals of pressure to the lid. The compressed samples are conditioned according to the temperatures and times shown in Table 3. The Initial Opening Force value shown in Table 3 is determined according to the Opening Force Test, wherein the Opening Force is measured 15 minutes after the adhesive shown in Table 3 is applied to the sample. Similarly, the 7-day and 14-day Opening Forces are measured 7 days and 14 days, respectively, after the application of the adhesive.

TABLE 3

| Sample | Adhesive | Initial Opening Force | 7-day Opening Force After Aging At Room Temperature (N) | 14-Day Opening Force After Aging At 38° C. (N) | 14-Day Opening Force After Aging At 50° C. (N) | Hook Type | Adhesive Amount (mg) |
|---|---|---|---|---|---|---|---|
| 1 | PHO-3005 | — | 1.1 | — | 1.7 | 963 | 0.25 |
| 2 | PHO-3005 | — | 2.3 | — | 2.6 | 963 | 0.25 |
| 3 | PHO-3005 | — | 2.7 | — | 2.0 | 732 | 0.25 |
| 4 | PHO-3000 | 1.9 | 1.4 | — | 3.8 | None | 1 |
| 5 | PHO-3000 | — | 1.4 | 1.4 | — | 88-1 | 1 |
| 6 | PHO-3000 | — | 2.0 | 2.2 | — | 963 | 2 |
| 7 | H2401 | — | 3.9 | 4.4 | — | 88-1 | 1 |
| 8 | H2401 | — | 4.3 | 5.7 | — | 963 | 2 |

As can be seen from Table 3, only the PHO-3005 fugitive adhesive provides suitable bond strength characteristics when compressed and subjected to a temperature of 50° C. The permanently bonding H2401 shows an increase in bond strength when aged at 38° C.

Test Methods

Unless otherwise indicated, all test methods and material or sample conditioning are performed at a temperature of 23° C.±2° C. and a relative humidity of 50%±2%.

Opening Force Test.

This method may be used for measuring the opening force of a first substrate bonded to a second substrate by determining the amount of force required to separate the substrate surfaces that are bonded to one another. The Opening Force Test is used to determine the Initial Opening Force value of a pair of bonded substrates by testing the pair of bonded substrates 15 minutes after the substrates are bonded to one another. The Opening Force Test is also used to determine the Aged Opening Force value of a pair of bonded substrates by testing the pair of bonded substrates more than 72 hours after the substrates are bonded to one another. The surface of a substrate that is opposite a bonded surface of that substrate is referred to in this method as a non-bonded surface. In certain embodiments, such as those including a folded substrate, the first substrate may be unitary with the second substrate. While this method may describe various exemplary configurations for bonded substrates, such as a diaper ear and/or fastening tab, it is to be understood that one of ordinary skill in the art could readily adapt this method to test the opening force of any bonded substrate.

The opening force of a bonded pair of substrates is measured using an MTS Alliance with TestWorks 4 software available from MTS Systems Corp., Eden Prairie, Minn., or equivalent, fitted with a suitable load cell. The load cell should be selected such that the maximum force attained in the test is between with 10% and 90% of the stated maximum load of the load cell. The jaws of the tensile tester must have flat surfaces and must be at least 25 mm wide. Also, the jaws should provide adequate force to ensure that the sample does not slip during testing. Additional details regarding suitable test apparatus, calibration procedures, etc. are given in ASTM D76-99 (Standard Specification for Tensile Testing for Textiles).

Figure 14A:
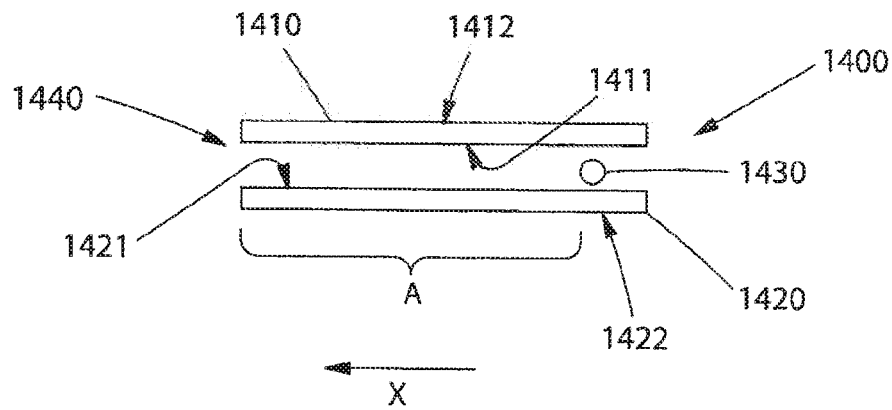
FIGS. 14A-14C are schematic cross-section views of a sample preparation for the Opening Force Test.
Figure 14B:
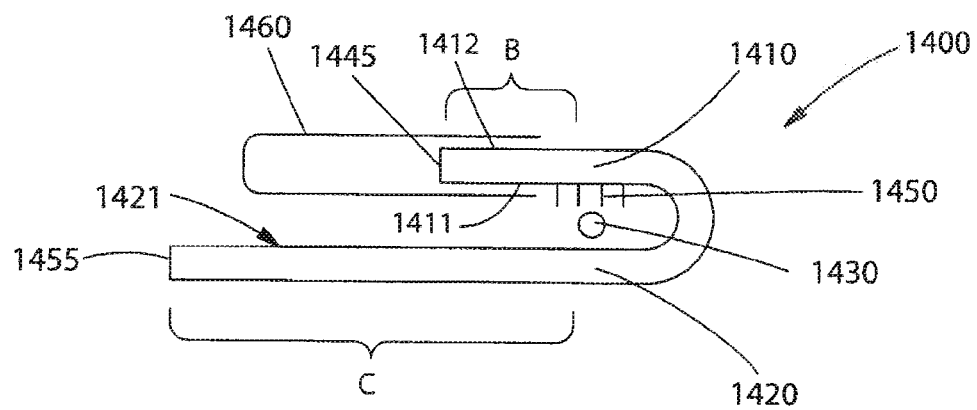
Figure 14C:
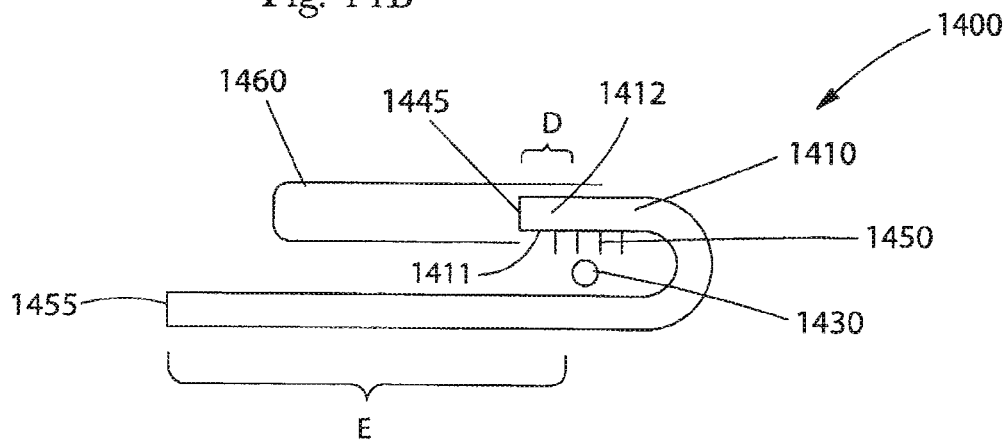

Sample Preparation:

1. If the bonded portion of the first and second substrates is incorporated into a finished product, carefully remove first and second substrates from the article (e.g., by cutting with scissors) while ensuring that there is substantially no peel or shear load on the bond to be tested.
2. If the sample contains exposed adhesive that is not a part of the bond between the first and second substrates, care must be taken to avoid allowing this adhesive to introduce artifacts into the data. Exposed adhesive should be deactivated, for example, by lightly coating it with talc or corn starch.
3. If either of the first or second substrates is extensible, render it substantially inextensible by applying backing tape (e.g., masking tape sold under the product code 410 by 3M) over the entire non-bonded surface of the material.
4. If the first and second substrates each extend at least 50 mm outwardly (e.g., in the x-direction as shown in FIG. 3, or otherwise in a direction parallel to the lateral axis for other embodiments) from the bond, then proceed to testing as detailed below. These extending portions are referred to as "tails." If the first and second substrates do not each have a tail that is at least 50 mm long, then add a leader made from standard, office masking tape such as SCOTCH 2600 brand masking tape available from 3M to the first and/or second sample substrate to provide the requisite tail. To attach a leader, perform the following. Secure a leader to the non-bonded surface of the substrate such that the leader will extend at least 50 mm from the bond when the leader is folded back onto itself, for example, as shown in FIGS. 14A-14C. Fold the leader back onto itself and join it to the bonded surface of the substrate such that at least 5 mm of the leader overlaps itself and the bonded surface. However, in any sample in which the bond is less than 10 mm from the relevant substrate edge, do not overlap the leader and the bonded surface of the substrate (i.e., only join the leader to itself). FIG. 14A shows an example of a sample 1400 prepared without an added leader. The sample 1400 includes a first substrate 1410 having a bonded surface 1411 and a non-bonded surface 1412. The first substrate 1410 is bonded to a second substrate 1420, which has a bonded surface 1421 and a non-bonded surface 1422. The first and second substrates 1410 and 1420 extend in the x-direction and are joined to one another by a bond 1430 (e.g., a frangible bond). As shown is FIG. 14A, the distance from the bond 1430 to the edge 1440 of the sample 1400 is greater than 50 mm. Thus, no leader is needed for the sample 1400 shown in FIG. 14A. FIG. 14B shows an example of a sample 1400 prepared with an overlapping leader. In FIG. 14B, the exemplary sample 1400 includes a first and second substrate 1410 and 1420, respectively, that are unitary. The first substrate 1410 includes engaging elements 1450. The first substrate 1410 is joined to the second substrate 1420 by the bond 1430 between the engaging elements 1450 and the bonded surface 1421 of the second substrate 1420. Since the distance between the edge of the first substrate 1410 and the edge of the bond 1430 is greater than 10 mm but less than 50 mm as shown in FIG. 14B, a leader

1460, which overlaps itself and the first substrate 1410, is affixed to the first substrate 1410. FIG. 14C shows an example of a sample prepared with no overlap of the leader and the first surface. Since the distance between the edge of the first substrate 1410 and the edge of the bond 1430 is less than 10 mm as shown in FIG. 14C, a leader 1460, which overlaps itself but not the first substrate 1410, is affixed to the non-bonded side 1412 of the first substrate 1410.

5. If the sample extends more than 25 mm in the y-direction (e.g., as shown in FIG. 3) beyond the y-direction ends of the bond, the excess material is to be removed (e.g., cut off) in a manner which places substantially no shear or peel load on the bond to be tested.

Opening Force Testing of Prepared Sample.

1. Set the spacing of the tensile testers' jaws (gauge length), such that the jaws of both clamps are at least 25 mm from the edge of the bond, when the sample is mounted with a tail in each of the upper and lower jaws, and with the bonded portion extending laterally midway between the jaws. Position the sample in the jaws such that there is no substantial shear or peel force being applied to the bond to be tested. In addition, position the sample such that there is substantially equal distance between the bond and the upper and lower jaws.
2. Insert the tails into the respective jaws and ensure that the tails are centered in the jaws with no portion of the sample or leader extending beyond the grip. The sample should not be under tension, but should have minimal slack.
3. Ensure that the grips are suitably tight to prevent slippage, and zero the crosshead location.
4. Initiate the test at a crosshead speed of 305 mm/minute with collected into a data file at a resolution of approximately 10 data points per mm.
5. Data collection is to stop either 10 mm of crosshead travel after the bond is broken or immediately prior to encountering any obstruction which would obscure determining the force to break the bond. For example, an obstruction could be the fold of a folded tape tab or an unrelated bond between the first and second substrates such as a bond fusing the two substrates together.
6. If a leader tears or delaminates from the substrate to which it is attached prior to the bond breaking and the peak load force is greater than 8 N, then record the observed peak load force. If a leader tears or delaminates from the substrate to which it is attached prior to the bond breaking and the peak load force is not greater than 8N, then discard the data and retest using a new sample, which has been reinforced by applying backing tape as described above.
7. Repeat the test until 10 samples have been successfully tested. Record the individual peak load forces and average them to obtain the Initial Opening Force value or Aged Opening Force value, as appropriate.

Modified Opening Force Test

This method may be used for measuring the Initial and Aged Modified Opening Forces of a first substrate bonded to a second substrate in a finished product such as is typically purchased by a consumer from a retail store. This method is substantially the same as the Opening Force Test above, with the following changes.

Sample Preparation:

Prepare a sample as indicated above in the Opening Force Test. Pre-heat a hot plate by setting the surface temperature of the hot plate to 50° C. Transfer the sample onto the hot plate and apply pressure to the sample by placing a 12.5 mm thick, 50 mm×50 mm polycarbonate square over the sample, such that the polycarbonate square is centered over the portion of the sample comprising the bonding agent, and apply weight until a total of 1 kg is present. Allow the sample to remain on the hot plate for 10 minutes. For measuring Initial Modified Opening Force, remove the sample from the hot plate and condition it for 15 minutes. Test the sample as described in the Opening Force Test method 15 minutes after removing it from the hot plate. For measuring Aged Modified Opening Force, remove the sample from the hot plate and condition it for 72 hours and then test the sample as described in the Opening Force Test method. Ten samples are tested and the individual peak load forces are averaged to obtain the Initial or Aged Modified Opening Force value.

Coupon Peel Test

The object of this test is to measure the change in bond strength of a particular bonding agent over time as observed on a particular substrate. This method may be used to test the bond strength provided by a bonding agent harvested from a finished product or a virgin bonding agent (i.e., a bonding agent that has not been incorporated into an article).

Harvested Adhesive: Using a razor blade, small spatula, thermal knife, or other suitable tool, carefully remove adhesive to be tested from a finished product and place into a suitable container (e.g., by scraping or melting the adhesive off of the finished product and into a container such as a laboratory weigh boat or glass container). Care should be taken to minimize inclusion of substrate fragments, fastener fragments, or other contaminants in the sample to be tested. Check the sample prior to testing and remove any contaminants which may be present. Obtain sufficient adhesive to perform the test below (e.g., approximately 50 mg or 0.56 g per test run, depending on the test).

Virgin Adhesive: virgin adhesive obtained from a supplier may require homogenization before testing if the outer wrap is part of the adhesive formulation, which is not uncommon. If this is the case, melt the adhesive and wrapper together at 175° C. in the lab-oven. Stir the adhesive from time to time with a metal spatula by hand to homogenize. After homogenization pour the adhesive onto silicone-treated release paper and let it cool down to ambient temperature. If the adhesive does not require homogenization, then proceed directly to the test procedure.

Procedure

1. Prepare cut samples of 2 mil corona-treated PET film (polyethylene terephtalate) film (commercially available from Filmquest Group Inc, Bolingbrook, Ill. USA) by cutting the film into rectangular pieces of 65×100 mm.
2. Obtain two, flat, aluminum plates (12.7±2 mm thickness) and having dimensions of 150 mm×305 mm.
3. Pre-heat a Carver Press (e.g., model 3853-0 available from Carver Inc., Wabash, Ind. USA) and the two aluminum plates to 177° C. Stack the two aluminum plates one on top of the other with edges aligned on the bottom platen of the press and close the press to 345 MPa+/−690 kPa.
4. Pre-weigh 0.035-0.045 g of the harvested or virgin adhesive into a laboratory weigh boat or other suitable container
5. Obtain release paper (e.g., 40-pound release liner commercially available from American Coated Products, Zionsville, Ind. USA) sized such that the PET film samples can be placed entirely within the bounds of the release paper, but the release paper does not extend past the edges of the aluminum plates. Place a strip of the PET film corona-treated side up onto the release-coated side of a sheet of the release paper. Pour or place the adhesive onto the center of the PET film. Use a metal spatula to center the adhesive on the film.
6. Place a second strip of the PET film on top of the adhesive such that the corona-treated side of the PET film faces the adhesive. Place a second layer of release paper, release-coated side down, on top of the PET film-adhesive sandwich
7. Open the Carver press' platens sufficiently to remove the top aluminum plate, while leaving the bottom aluminum plate on the bottom platen of the press
8. Place the sample from step 5 onto the bottom aluminum plate, taking care to avoid dislocating the adhesive from its original position between the PET film layers.
9. Place the top aluminum plate on top of the paper-PET-adhesive sandwich disposed on the bottom aluminum plate. Use care to keep the sandwich of materials horizontal and avoid displacing the release paper and PET film in a way that could displace the adhesive from between the layers of PET film.
10. Close the Carver press platen to a pressure of 345 MPa+/−690 kPa. Wait 20 seconds. Then open the press to a sufficient gap to remove the stacked aluminum plates with the material sandwich still positioned between them. Again, keep the plates horizontal and use care to avoid displacing the release paper and PET film.
11. Gently remove the top plate and place the release paper-PET film-adhesive sandwich onto a horizontal room temperature surface.
12. Allow the sample to cool for at least 10 minutes but not more than 30 minutes then use a razor to cut just the PET/Adhesive sandwich into a 25 mm wide test specimen centered within the 65 mm PET width. The final test specimen is therefore 25×100 mm. Use care to avoid debonding the adhesive from the PET layers.
13. The peel force of the PET/Adhesive sandwich is measured using an MTS Alliance with TestWorks 4 software available from MTS Systems Corp., Eden Prairie, Minn., or equivalent, fitted with a suitable load cell. The load cell should be selected such that the maximum force attained in the test is between with 10% and 90% of the stated maximum load of the load cell. The jaws of the tensile tester are selected to have flat surfaces and are at least 25 mm wide. Also, the jaws should be configured or selected to provide adequate force to ensure that the sample does not slip during testing. Additional details regarding suitable test apparatus, calibration procedures, etc. are given in ASTM D76-99 (Standard Specification for Tensile Testing for Textiles).
14. Set the spacing of the tensile testers' jaws (gauge length) to 60+/−1 mm. Set the cross-head speed to 5.0 mm/min.
15. Mount the sample in the jaws of the tensile tester such that one PET strip is clamped in the top jaw and the other strip is clamped in the bottom jaw. Use the unbounded ends of the PET strips to do this while using care to avoid de-bonding the center of the strips from the adhesive. The sample should not be under tension, but should have minimal slack.
16. Ensure that the grips are suitably tight to prevent slippage, and zero the crosshead location.
17. Initiate the test at a crosshead speed of 5 mm/minute with collected into a data file at a resolution of approximately 10 data points per mm.
18. Data collection is to stop after the adhesive to PET bond is broken completely. Report the peak load during the test
19. Repeat the test until at least 3 samples have been successfully tested. Record the individual peak load forces and average them to obtain the Average Peel Force.

Rheological Measurement Test

The object of this test is to determine the crossover temperature of a composition. This method may be used to test an adhesive sample harvested from a finished product or a virgin adhesive sample. Refer to the Coupon Peel Test above for preparing virgin and harvested adhesive samples.

Equipment:
  Air-circulating lab-oven or chamber capable to be controlled up to 200° C. (+/−3° C.) (e.g., Carbolite air circulating oven, Peak series, model PF60 with temperature control unit Eurotherm 2416CC)
  Lab-Balance which allows precision of 0.01 g (e.g., Mettler PG503-S or equivalent)
  TA Instruments Advanced Rheometer series AR2000 with Peltier temperature option, TA Instruments Corporation, New Castle, Del.; with 25 mm flat parallel plate geometry consisting of an upper steel plate (diameter: 25 mm) and a lower Peltier or heating plate enabling temperature control. The rheometer is capable of applying temperatures of from −5° C. to 170° C. with a precision of 0.5° C. and torques up to 200 milliNewton meters (mNm) with a precision of 0.1 mNm.

Test Procedure:
Geometry Gap Setting:
  1. Set the temperature of the Peltier or heating plate of the rheometer to 120° C.
  2. Calibrate the zero gap at 120° C.
  3. Set the geometry gap to 2000 micrometers.
  4. Weigh out 0.56 g+/−0.01 g of adhesive and place it onto the center of the Peltier or heating plate of the rheometer and set the temperature to 120° C.
  5. After approximately ⅔ of the amount of adhesive is molten, slowly lower the upper plate to the geometry gap of 2000 micrometer. The velocity of the rheometer head must not exceed 1000 micrometers per second in order to achieve good contact between the adhesive and the upper plate without damaging the adhesive sample.
  6. Cover the geometry with the geometry cover—i.e., solvent trap cover—for 2 minutes so that the upper plate can heat up and the adhesive gets completely molten.
  7. Remove the cover and rotate the upper plate manually to distribute the adhesive evenly between the upper plate and the Peltier or heating plate. Ensure full contact of the adhesive to the upper plate. Afterwards cover the geometry again for another 2 minutes.
  8. Remove the cover and check whether the adhesive is distributed evenly. If it is not, repeat point 7. If it is, cover the geometry again and continue with point 9.
  9. Perform a pre-shearing at a frequency of 2.5 radians per second and an oscillatory strain amplitude of 1% for 4 minutes to condition the adhesive.
  10. After pre-shearing keep the temperature at 120° C. for 1 minute to let the adhesive settle and recover from pre-shearing.
  11. Ensure the geometry and adhesive are thermally equilibrated by maintaining the setup at 120° C. for more than 2 minutes without any application of stress.

Temperature Sweep Execution:
Perform a temperature sweep starting at 120° C. and cooling down to −5° C. at a cooling rate of 3° C. per minute. Set the frequency to 10 radians per second and the commanded oscillatory strain amplitude to 26%. The apparent storage modulus (G'), apparent loss modulus (G") and the apparent loss tangent (Tan δ) are recorded as a function of temperature. Note that the commanded strain may not be achieved, especially at lower temperatures, and that the strain may exceed the linear elastic region of the adhesive composition. The apparent values are the respective values recorded by the instrument notwithstanding these conditions.

Calculation/Reporting:

From the temperature sweep report the following parameters: cross-over temperature in ° C. (1 decimal place). The cross-over-temperature is found at the end of the rubber-plateau towards higher temperatures indicating the beginning of the terminal zone. At the cross-over temperature, the apparent storage modulus and apparent loss modulus values are equal and the apparent loss tangent value is 1.

Shear Test.

The object of this method is to measure the bond strength of an engaged hook/loop type mechanical fastener by applying a force to the engaged hook and loop materials of the fastener, wherein the force is applied in a direction parallel to the plane of the fastener. The substrate comprising the hooks is referred to as the hook material and the substrate comprising the loops is referred to as the receiving member.

The hook material is mounted to a leader made from heavyweight resume paper having a basis weight of approximately 120 gsm using 3M Medical Products #1524 double-sided tape to join the non-engaging side of the hook material to the leader to form a test specimen having the hooks at one end with the tail of the leader extending at least 50 mm beyond the hooks, as described above in the Opening Force Test method and shown in FIG. 14A. Test specimens are cut to 25 mm length (y-direction in FIG. 3 corresponds to length). For the treated samples (i.e., samples with a bonding agent applied to them), the sample is cut such that the bonding agent is approximately centered in the 25 mm length. The receiving member is affixed, functional side up, over its entire surface to a steel plate (50 mm×75 mm×1.5 mm) using 3M 410 double-sided tape such that the receiving member is centered on plate and parallel to the long dimension of the plate. The hook material is placed onto the receiving member such that the lateral direction (x-direction in FIG. 3) is aligned with the lateral direction of the receiving member (as though the receiving member were on the article of FIG. 1). Using thumb or forefinger, press the hook into the receiving member with just sufficient pressure to affix them together. To engage the hooks into the receiving member, an 11 pound steel roller, 58 mm wide, is rolled back and forth over the sample 5 times in each of the forward and backward directions. Each back and forth stroke should take about two seconds, and care should be taken to ensure the roller stays on the plate while rolling. A first edge of the steel plate is placed into the lower grip of a tensile tester with the tail of the leader extending upward toward and into an open (untightened) upper grip of the tensile tester. The lower grip is tightened. The upper grip is then tightened such that there is substantially no tension on the leader or fastening system once the upper grip is tightened. The tensile tester is set to separate the grips at a rate of 305 mm/minute and collect data at a frequency of at a resolution of approximately 10 data points per mm. The test is initiated such that the upper grip pulls on the leader which applies load to the engaged hook/loop specimen. Data are recorded until the hook and loop bond fails or the leader tears. The peak load that occurs is recorded in Newtons. For each type of sample (treated and untreated), 10 specimens are run. The Treated Shear value is obtained by averaging the peak load of the treated samples, and the Untreated Shear value is obtained by averaging the peak load of the untreated samples.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising:
   a mechanical fastening system comprising first and second opposing surfaces, a web, and at least one engaging member joined to the web; and
   a frangible bonding agent disposed on a first portion of the first surface of the fastening system;
   wherein the engaging member includes a plurality of engaging elements and the web includes a plurality of receiving elements that are engageable with the engaging elements;
   wherein the frangible bonding agent is disposed on one or more of the engaging elements;
   wherein the frangible bonding agent is disposed on the engaging elements such that a first group of engaging elements has the frangible bonding agent disposed thereon and a second group of engaging elements is substantially free of the frangible bonding agent, the first group of engaging elements being substantially surrounded by the second group of engaging elements.

2. The disposable absorbent article of claim 1, wherein the fastening system is engaged and has an Initial Opening Force value of greater than about 2 N according to the Opening Force Test.

3. The disposable absorbent article of claim 2, wherein the Initial Opening Force value is greater than about 5 N.

4. The disposable absorbent article of claim 2, wherein the Initial Opening Force value is greater than about 8 N.

5. The disposable absorbent article of claim 1, wherein the fastening system is engaged and has an Aged Opening Force value of less than about 8 N.

6. The disposable absorbent article of claim 5, wherein the Aged Opening Force value is less than about 5 N.

7. The disposable absorbent article of claim 5, wherein the Aged Opening Force value is less than about 2 N.

8. The disposable absorbent article of claim 1, wherein the fastening system is engaged and has an Initial Modified Opening Force value and an Aged Modified Opening Force, value the Aged Modified Opening Force value being no more than about 1.3 times greater than the Initial Modified Opening Force value according to the Modified Opening Force Test.

9. The disposable absorbent article of claim 8, wherein the Aged Modified Opening Force value is less than about 1.6 times greater than the Initial Modified Opening Force value.

10. The disposable absorbent article of claim 8, wherein the Aged Modified Opening Force value is less than about 1.1 times greater than the Initial Modified Opening Force value.

11. The disposable absorbent article of claim 8, wherein the Aged Modified Opening Force value is about the same as the Initial Modified Opening Force value.

12. The disposable absorbent article of claim 8, wherein the Aged Modified Opening Force value is less than the Initial Modified Opening Force value.

13. The disposable absorbent article of claim 1, wherein the fastening system is engaged and has an Initial Modified Opening Force value of greater than about 2 N according to the Modified Opening Force Test.

14. The disposable absorbent article of claim 13, wherein the Initial Modified Opening Force value is greater than about 5 N.

15. The disposable absorbent article of claim 13, wherein the Initial Modified Opening Force value is greater than about 8 N.

16. The disposable absorbent article of claim 1, wherein the fastening system is engaged and has an Aged Modified Opening Force value of less than about 8 N according to the Modified Opening Force Test.

17. The disposable absorbent article of claim 16, wherein the Aged Modified Opening Force value is less than about 5 N.

18. The disposable absorbent article of claim 16, wherein the Aged Modified Opening Force value is less than about 2 N.

19. The disposable absorbent article of claim 16, wherein the Aged Modified Opening Force value is less than about 1 N.

20. The disposable absorbent article of claim 1, wherein at least a portion of the fastening system is folded such that the frangible bonding agent contacts a second portion of the first surface of the fastening system and forms a bond between the first and second portions of the first surface.

21. The disposable absorbent article of claim 20, wherein the fastening system includes a folded fastening tab and the engaging member is disposed on the folded fastening tab.

22. The disposable absorbent article of claim 1, wherein the frangible bonding agent is an adhesive.

23. The disposable absorbent article of claim 22, wherein the adhesive is a fugitive hot-melt adhesive.

24. The disposable absorbent article of claim 1, wherein the frangible bonding agent spans a gap between the engaging elements.

25. The disposable absorbent article of claim 1, wherein the frangible bonding agent is disposed on one or more of the receiving elements.

26. The disposable absorbent article of claim 1, wherein the engaging member is joined to the fastening system at a base and the frangible bonding agent is not disposed on the base.

27. The disposable absorbent article of claim 1, wherein the frangible bonding agent is contiguous with at least one edge of the first surface of the fastening system.

28. The disposable absorbent article of claim 1, wherein the frangible bonding agent is present in a pattern selected from the group consisting of one or more substantially straight lines, an s-shape, a z-shape, a c-shape, a broken line, a t-shape, a cross-shape, spiral-shape, omega-shape, dots and combinations of these.

29. The disposable absorbent article of claim 1, wherein the fastening system has a Treated Shear value and an Untreated Shear value, the treated Shear value being at least about 50% of the untreated Shear value according to the Shear Test.

30. The disposable absorbent article of claim 29, wherein the Treated Shear value is at least about 80% of the Untreated Shear value.

31. The disposable absorbent article of claim 29, wherein the Treated Shear value and the Untreated Shear value are substantially the same.

32. The disposable absorbent article of claim 29, wherein the Treated Shear value is less than the Untreated Shear value.

* * * * *